United States Patent
Lim et al.

(10) Patent No.: US 8,946,237 B2
(45) Date of Patent: Feb. 3, 2015

(54) PYRAZOLO[1,5-A]PYRIMIDINES AS MARK INHIBITORS

(75) Inventors: Jongwon Lim, Lexington, MA (US); Brandon M. Taoka, Hoboken, NJ (US); Sandra Lee, Princeton, NJ (US); Alan Northrup, Reading, MA (US); Michael D. Altman, Needham, MA (US); David L. Sloman, Boston, MA (US); Matthew G. Stanton, Marlton, NJ (US); Njamkou Noucti, Carrboro, NC (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 292 days.

(21) Appl. No.: 13/521,382

(22) PCT Filed: Jan. 11, 2011

(86) PCT No.: PCT/US2011/020739
§ 371 (c)(1),
(2), (4) Date: Apr. 3, 2013

(87) PCT Pub. No.: WO2011/087999
PCT Pub. Date: Jul. 21, 2011

(65) Prior Publication Data
US 2013/0210838 A1   Aug. 15, 2013

Related U.S. Application Data

(60) Provisional application No. 61/294,902, filed on Jan. 14, 2010.

(51) Int. Cl.
*A01N 43/90* (2006.01)
*A61K 31/519* (2006.01)
*C07D 487/00* (2006.01)
*C07D 487/04* (2006.01)

(52) U.S. Cl.
CPC .................................. *C07D 487/04* (2013.01)
USPC ........................................ 514/259.3; 544/281

(58) Field of Classification Search
None
See application file for complete search history.

(56) References Cited

U.S. PATENT DOCUMENTS 7,151,109 B2   12/2006   Fu
8,592,425 B2   11/2013   Altman et al.

FOREIGN PATENT DOCUMENTS

WO   WO2007/085873   8/2007
WO   WO2009/014620   1/2009

OTHER PUBLICATIONS

Greshock et al.; "Leucine-Rich Repeat Kinase Enzyme Activity"; U.S. Appl. No. 13/880,992, filed Oct. 25, 2011.
International Search Report, International Application No. PCT/US11/20739, Date of Mailing Mar. 23, 2011.
Knowles et al.; " Pyrazolo[1,5-A]Pyridines as Mark Inhibitors"; U.S. Appl. No. 13/057,510, filed Jul. 27, 2009.
Panneerselvam' "Crysal structure of the catalytic and ubiquitin-associated domains of the protein kinase" MARK2/PAR-1 from *Rattus norvigicus* Ph.D. Thesis [online]Jan. 6, 2006; pp. 14, 56-67, 78-82.

*Primary Examiner* — Jeffrey H Murray
(74) *Attorney, Agent, or Firm* — Keith D. MacMillan; John C. Todaro

(57) ABSTRACT

The invention encompasses pyrazolo[1,5-a]pyrimidine derivatives which selectively inhibit microtubule affinity regulating kinase (MARK) and are therefore useful for the treatment or prevention of Alzheimer's disease. Pharmaceutical compositions and methods of use are also included.

11 Claims, 2 Drawing Sheets

PYRAZOLO[1,5-A]PYRIMIDINES AS MARK INHIBITORS

BACKGROUND OF THE INVENTION

Alzheimer's disease (AD) is the most common cause of dementia in the elderly and is characterised by a decline in cognitive function, that progresses slowly and results in symptoms such as memory loss and disorientation. Death occurs, on average, 9 years after diagnosis. The incidence of AD increases with age, so that while about 5% of people over the age of 70 are sufferers, this figure increases to 20% of those over 80 years old.

Existing treatments exclusively target the primary symptoms of AD. Diseased neurons may release insufficient or excessive amounts of particular neurotransmitters, and so current drugs are aimed at increasing neurotransmitter levels or at reducing the stimulation of nerve cells by neurotransmitters. Although these drugs provide some improvement in the symptoms of AD, they fail to address the underlying cause of the disease.

The classic clinical and neuropathological features of AD consist of senile or neuritic plaques and tangled bundles of fibers (neurofibrillary tangles) [Verdile, G., et al, Pharm. Res. 50:397-409 (2004)]. In addition, there is a severe loss of neurons in the hippocampus and the cerebral cortex. Neuritic plaques are extracellular lesions, consisting mainly of deposits of β-amyloid peptide (Aβ), surrounded by dystrophic (swollen, damaged and degenerating) neurites and glial cells activated by inflammatory processes. In contrast, neurofibrillary tangles (NFTs) are intracellular clusters composed of a hyperphosphorylated form of the protein tau, which are found extensively in the brain (e.g. mainly in cortex and hippocampus in AD). Tau is a soluble cytoplasmic protein which has a role in microtubule stabilisation. Excessive phosphorylation of this protein renders it insoluble and leads to its aggregation into paired helical filaments, which in turn form NFTs.

The amyloid cascade hypothesis proposes that abnormal accumulation of Aβ peptides, particularly Aβ42, initiates a cascade of events leading to the classical symptoms of AD and ultimately, to the death of the patient. There is strong evidence [e.g. Rapoport, M., et al (2002) Proc. Natl. Acad. Sci USA 99:6364-6369] that dysregulation of tau function is a key step in the cascade of Alzheimer's disease pathology leading ultimately to neuronal death. Furthermore, tau mutations and NFTs are found in other dementias in which Aβ pathology is absent, such as frontotemporal dementia, Pick's disease and parkinsonism linked to chromosome 17 (FTDP-17) [Mizutani, T. (1999) Rinsho Shikeigaku 39: 1262-1263]. Also, in AD the frequency of NFTs correlates to the degree of dementia better than that of senile plaques [Arriagada, P. V., et al (1992) Neurology 42:631-639], while significant numbers of amyloid plaques are often found in the brains of non-demented elderly people, suggesting that amyloid pathology on its own is not sufficient to cause dementia. For these reasons, normalisation of tau function (in particular prevention of hyperphosphorylation) is seen as a desirable therapeutic goal for the treatment of AD and other dementing conditions.

Tau is a 352-441 amino acid protein encoded by the Mapt (Microtubule-associated protein tau) gene which is widely expressed in the central nervous system (CNS) with localisation primarily in axons [Binder et al J. Cell Biol. 1985, 101(4), 1371-1378]. The major function of tau is regulation of the stability of microtubules (MTs), intracellular structural components comprised of tubulin dimers which are integral in regulating many essential cellular processes such as axonal transport and elongation as well as generation of cell polarity and shape. Tau binding to tubulin is a key factor in determining the rates of polymerisation/depolymerisation (termed dynamic instability) of MTs, and tau is therefore key to the regulation of many essential cellular processes [see, for example, Butner, K. A., Kirschner, M. W. (1991) J. Cell. Biol. 115: 717-730].

Tau is a basic protein with numerous serine and threonine residues, many of which are susceptible to phosphorylation. While normal tau has two to three phosphorylated amino acid residues, hyperphosphorylated tau found in AD and other tauopathies typically has eight or nine phosphorylated residues. A variety of kinases promote phosphorylation of these sites, including proline-directed kinases such as glycogen synthase kinase 3β (GSK3β) and cyclin dependent kinase 5 (cdk5), and non-proline-directed kinases such as protein kinase A (PKA) and calmodulin (CaM) kinase II, which phosphorylate tau at Lys-(Ile/Cys)-Gly-Ser sequences, also known as KXGS motifs. One KXGS motif is found in each of the MT binding repeats. Phosphorylation at these sites is important for the regulation of tau-MT binding and while the degree of phosphorylation is normally low, it has been shown to be increased in brain tissue from AD patients. Phosphorylation of one particular residue within the KXGS motifs, Ser-262 has been shown to be elevated in tau protein extracted from the NFTs in AD [Hasegawa, M. et al (1992) J. Biol. Chem 267:17047-17054] and phosphorylation at this site also appears to dramatically reduce MT binding [Biernat, J. et al. (1993) Neuron 11: 153-163]. Nishimura et al. [Cell 116: 671-682 (2004)] demonstrated that overexpression of the kinase PAR-1 in *Drosophila* led to enhanced tau-mediated toxicity and an increase in the phosphorylation of tau on Ser-262, Ser-356, and other amino acid residues, including sites phosphorylated by GSK3β and Cdk5. Their findings suggest that PAR-1 kinase acts as a master kinase during the process of tau hyperphosphorylation, with the phosphorylation of the Ser-262 and Ser-356 sites being a prerequisite for the subsequent phosphorylation at downstream sites by other kinases.

The mammalian ortholog of PAR-1 is microtubule affinity-regulating kinase (MARK). There are four MARK isoforms and these form part of the AMP-dependent protein kinase (AMPK) family. Like PAR-1, MARK is thought to phosphorylate tau, perhaps in response to an external insult, such as the disruption of $Ca^{2+}$ homeostasis caused by Aβ, priming it for further phosphorylation events. It is not clear whether the phosphorylation of tau by MARK leads directly to its detachment from MTs or the subsequent phosphorylation events cause detachment. The resulting unbound, hyperphosphorylated tau is delocalised to the somatodendritic compartment and is then cleaved by caspases to form fragments prone to aggregation [Drewes, G. (2004). Trends Biochem. Sci 29:548-555; Gamblin, T. C., et al, (2003) Proc. Natl. Acad. Sci. U.S.A. 100:10032-10037]. These aggregates can grow into filaments, which are potentially toxic, eventually forming the NFTs found in AD.

For these reasons, it is proposed that MARK inhibitors will enable the prevention or amelioration of neurodegeneration in AD and other tauopathies.

This invention relates to methods and materials for the treatment or prevention of neurodegenerative diseases such as Alzheimer's disease. In particular, there is disclosed a particular class of pyrazolo[1,5-a]pyrimidine derivatives which selectively inhibit microtubule affinity regulating kinase (MARK).

WO 2009/014620 A1, published Jan. 29, 2009, describes a class of 6-heterocyclic substituted pyrazolo[1,5-a]pyrimidines as inhibitors of MARK. The present invention is directed to compounds having smaller substituents, such as halo, alkyl or ether groups, at the 6-position of the pyrazolo[1,5-a]pyrimidine core.

SUMMARY OF THE INVENTION

The invention encompasses pyrazolo[1,5-a]pyrimidine derivatives which selectively inhibit microtubule affinity regulating kinase (MARK) and are therefore useful for the treatment or prevention of Alzheimer's disease. Pharmaceutical compositions and methods of use are also included.

DETAILED DESCRIPTION OF THE INVENTION

Figure 1:
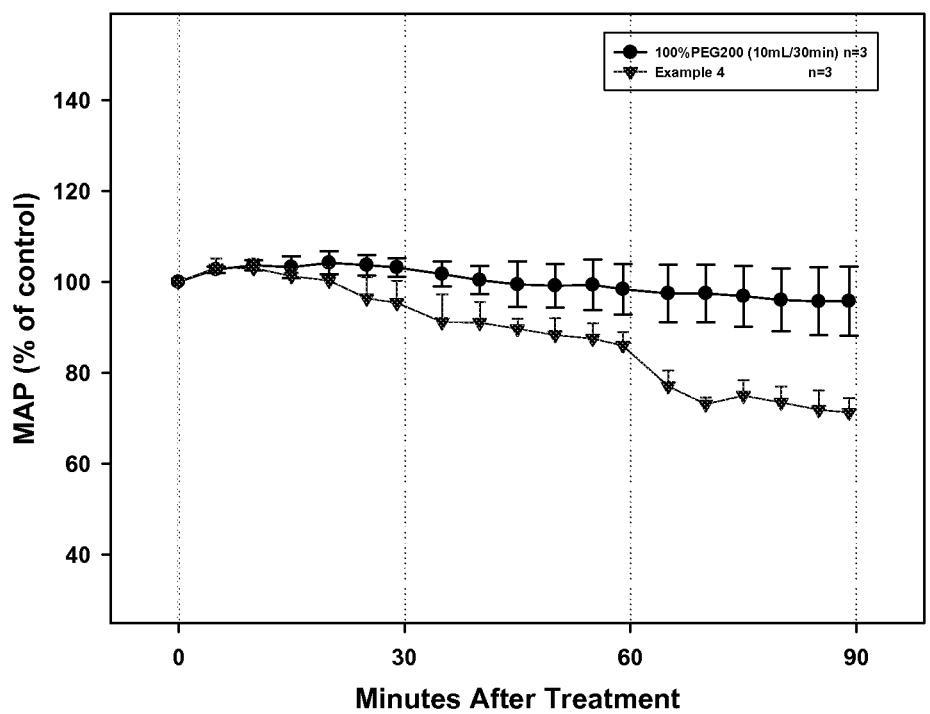
FIG. 1 illustrates that Example 4 lowered Mean Arterial Pressure by 25% when it was dosed at 5 mg/kg cumulatively over the course of 90 minutes in anesthetized dogs.
Figure 2:
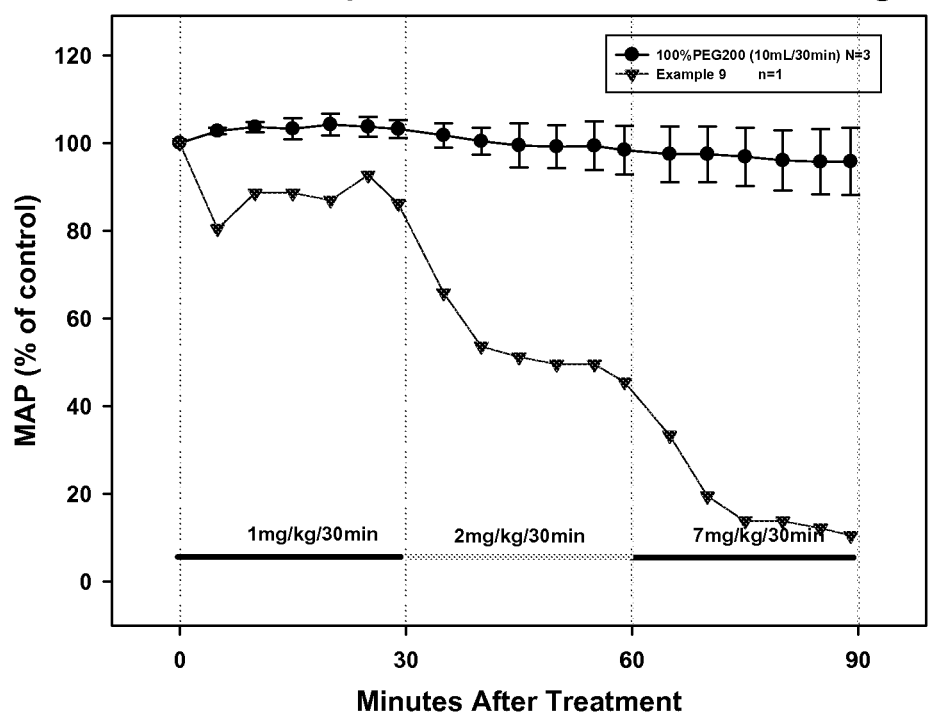
FIG. 2 illustrates that Example 9 lowered Mean Arterial Pressure by 89% when it was dosed at 10 mg/kg cumulatively over the course of 90 minutes in anesthetized dogs.

The invention encompasses a genus of compounds of formula I:

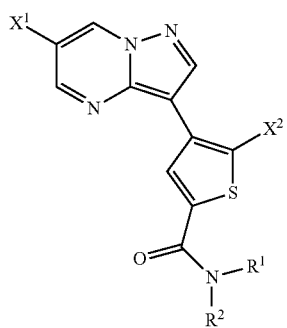

I or a pharmaceutically acceptable salt or hydrate thereof; wherein:

$X^1$ is selected from the group consisting of: H, halogen, $C_{1-6}$alkyl, $C_{2-6}$alkenyl, $C_{2-6}$alkynyl, $C_{3-6}$cycloalkyl, $C_{1-6}$alkoxy, —C(O)—O$C_{1-4}$alkyl, $C_{3-6}$cycloalkoxy, CN and $N(R^3)_2$, wherein said $C_{1-6}$alkyl, $C_{2-6}$alkenyl, $C_{2-6}$alkynyl, $C_{3-6}$cycloalkyl, $C_{1-6}$alkoxy, —C(O)—O$C_{1-4}$alkyl and $C_{3-6}$cycloalkoxy are optionally substituted up to the maximum number of substitutable positions with halogen;

$X^2$ is selected from the group consisting of: H, halogen, $C_{3-6}$cycloalkyl, $C_{1-6}$alkyl, $C_{2-6}$alkenyl, $C_{2-6}$alkynyl, $C_{3-6}$cycloalkenyl, —CN, nitro and $N(R^3)_2$; said $C_{1-6}$alkyl optionally substituted with up to 3 halogen atoms and said $C_{2-6}$alkenyl and $C_{2-6}$alkynyl optionally substituted with up to 3 $R^5$ groups;

$R^1$ represents H or $C_{1-4}$alkyl which is optionally substituted with OH, CN, $CF_3$, $C_{1-4}$alkoxy, amino, $C_{1-4}$alkylamino or di($C_{1-4}$alkyl)amino;

$R^2$ is selected from:
(i) H;
(ii) $C_{1-8}$alkyl or $C_{2-8}$alkenyl, either of which optionally bears up to 3 substituents independently selected from halogen, OH, CN, $CF_3$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and phenyl, said phenyl bearing 0 to 5 halogen substituents; and (iii) $C_{3-10}$cycloalkyl, $C_{3-10}$cycloalkyl$C_{1-4}$alkyl, Het, Het$C_{1-4}$alkyl, aryl or aryl$C_{1-4}$alkyl, any of which optionally bears up to 4 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$, $NR^3SO_2R^4$ and —P(O)—$(OR^3)_2$; where "aryl" refers to phenyl or 5- or 6-membered heteroaryl, either of which phenyl or heteroaryl is optionally fused to a 5- or 6-membered carbocycle or heterocycle, "Het" refers to a nonaromatic or partially aromatic mono- or bicyclic heterocyclic system of up to 10 ring atoms and $C_{3-10}$cycloalkyl and the cyclic portion of $C_{3-10}$cycloalkyl$C_{1-4}$alkyl may be fused with phenyl or a 5- or 6-membered heteroaryl;

or $R^1$ and $R^2$ together may complete a mono- or bicyclic heterocyclic system of up to 10 ring atoms which optionally bears up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$;

each $R^3$ independently represents H or $C_{1-6}$alkyl which is optionally substituted with up to 3 halogen atoms or with OH, CN, $CF_3$, $C_{1-4}$alkoxy, amino, $C_{1-4}$alkylamino or di($C_{1-4}$alkyl)amino;

$R^4$ has the same definition as $R^3$ except that $R^4$ is not H; and
$R^5$ is selected from the group consisting of: phenyl, hydroxy, $C_{3-6}$cycloalkyl, and $C_{1-4}$alkoxy.

Within the genus, the invention encompasses a first sub-genus of compounds of formula I wherein $X^2$ is $C_{1-4}$alkyl.

Within the first sub-genus, the invention encompasses a first class of compounds of formula I wherein $R^2$ is $C_{3-10}$cycloalkyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

Also within the first sub-genus, the invention encompasses a second class of compounds of formula I wherein $R^2$ is cyclohexyl bearing up to 3 substituents independently selected from halogen, OH, oxo, CN, $CF_3$, $R^4$, $OR^3$, $SR^4$, $SO_2R^4$, $SO_2N(R^3)_2$, $COR^3$, $CO_2R^3$, $CON(R^3)_2$, $N(R^3)_2$, $NR^3COR^4$ and $NR^3SO_2R^4$.

Also within the genus, the invention encompasses a second sub-genus of compounds having Formula Ia

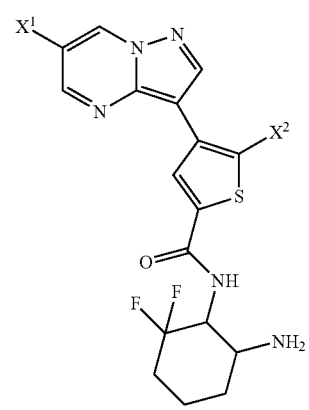

Ia or a pharmaceutically acceptable salt or hydrate thereof; wherein:

$X^1$ is selected from the group consisting of: halogen, $C_{1-6}$alkyl, $C_{3-6}$cycloalkyl, $C_{1-6}$alkoxy, —C(O)—O$C_{1-4}$alkyl and $C_{3-6}$cycloalkoxy, wherein said $C_{1-6}$alkyl and $C_{1-6}$alkoxy are optionally substituted up to the maximum number of substitutable positions with fluoro; and $X^2$ is halogen, methyl or ethyl.

Within the second sub-genus, the invention encompasses a third class of compounds of Formula Ia wherein: $X^1$ is selected from the group consisting of: chloro, methyl, trifluoromethyl, methoxy, difluoromethoxy, trifluoromethoxy, ethoxy, propoxy, isopropoxy, cyclopentyloxy, 2,2-difluoroethoxy, 2,2,2-trifluoroethoxy and methoxycarbonyl.

The invention also encompasses a compound selected from Examples 1 to 22 described below or a pharmaceutically acceptable salt of any of the foregoing compounds.

The invention also encompasses a pharmaceutical composition comprising a compound of formula I or a pharmaceutically acceptable salt or hydrate thereof, and a pharmaceutically acceptable carrier.

The invention further provides a method for treatment or prevention of a neurodegenerative disease associated with hyperphosphorylation of tau in a human patient, said method comprising administering to that patient an effective amount of a compound of formula I as defined above, or a pharmaceutically acceptable salt or hydrate thereof.

Neurodegenerative diseases associated with hyperphosphorylation of tau include AD, frontotemporal dementia, Pick's disease and parkinsonism linked to chromosome 17 (FTDP-17).

In a further aspect, the invention provides a method for reducing the production of hyperphosphorylated tau in a human patient, said method comprising administering to said patient an effective amount of a compound of formula I as defined above or a pharmaceutically acceptable salt or hydrate thereof.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine.

The expression "$C_{3-x}$cycloalkyl" as used herein, where x is an integer greater than 3, refers to nonaromatic hydrocarbon ring systems containing from 3 to x ring atoms. Said systems may be monocyclic or bicyclic if the magnitude of x allows it. Examples include cyclopropyl, cyclobutyl, cyclopentyl, cyclohexyl, cycloheptyl, bicycloheptyl and decalinyl.

The expression "$C_{3-x}$cycloalkenyl" as used herein, means "$C_{3-x}$cycloalkyl" as defined above but containing at least one double bond.

Unless indicated otherwise, the term "bicyclic" includes bridged bicyclic and spiro-linked ring systems as well as fused ring systems. However, a bicyclic system in which one or both rings are aromatic is of necessity a fused ring system.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, trifluoroacetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds useful in the invention have one or more asymmetric centres, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention and any chemical formulas, names and depictions herein, unless a specific stereochemistry is indicated otherwise.

When a compound useful in the invention is capable of existing in tautomeric keto and enol forms, both of said forms are considered to be within the scope of the invention. It will be apparent to those skilled in the art that a hydroxy substituent on an unsaturated ring may be capable of tautomerising to a ketone. In such circumstances, both tautomers are to be considered equivalent. Thus, for example, 2-hydroxypyridine is considered equivalent to 2-oxo-1,2-dihydropyridine.

A nitrogen atom forming part of a heteroaryl ring may be in the form of the N-oxide. A sulphur atom forming part of a nonaromatic heterocycle may be in the form of the S-oxide or S,S-dioxide.

A heteroaryl group may be attached to the remainder of the molecule via a ring carbon or a ring nitrogen, provided that this is consistent with preservation of aromaticity.

In the compounds of generic formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Specific examples of compounds in accordance with the invention are provided in the Examples hereinafter.

Where they are not themselves commercially available, the starting materials and reagents described above may be obtained from commercially available precursors by means of well known synthetic procedures and/or the methods disclosed in the Examples section herein.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds of formula I are suitably administered to patients in the form a pharmaceutical composition comprising the active ingredient (i.e. the compound of formula I or pharmaceutically acceptable salt or hydrate thereof) and a pharmaceutically acceptable carrier, and said pharmaceutical compositions constitute a further aspect of the invention.

Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

In one embodiment of the invention, the compound of formula I is administered to a patient suffering from AD, FTDP-17, Pick's disease or frontotemporal dementia, in particular AD.

In an alternative embodiment of the invention, the compound of formula I is administered to a patient suffering from mild cognitive impairment or age-related cognitive decline. A favourable outcome of such treatment is prevention or delay of the onset of AD. Age-related cognitive decline and mild cognitive impairment (MC1) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings,* 78 (2003), 1290-1308. In a study of elderly subjects, Tuokko et al (Arch, *Neurol.,* 60 (2003) 577-82) found that those exhibiting MCI at the outset had a three-fold increased risk of developing dementia within 5 years.

Grundman et al (*J. Mol. Neurosci.,* 19 (2002), 23-28) report that lower baseline hippocampal volume in MCI patients is a prognostic indicator for subsequent AD. Similarly, Andreasen et al (*Acta Neurol. Scand,* 107 (2003) 47-51) report that high CSF levels of total tau, high CSF levels of phospho-tau and lowered CSF levels of Aβ42 are all associated with increased risk of progression from MCI to AD.

Within this embodiment, the compound of formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42).

A genetic predisposition (especially towards early onset AD) can arise from point mutations in one or more of a number of genes, including the APP, presenilin-1 and presenilin-2 genes. Also, subjects who are homozygous for the ε4 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropsychological tests are known in the art for this purpose, such as the Mini-Mental State Examination (MMSE) with norms adjusted for age and education (Folstein et al., *J. Psych. Res.,* 12 (1975), 196-198, Anthony et al., *Psychological Med.,* 12 (1982), 397-408; Cockrell et al., *Psychopharmacology,* 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry,* 141 (1984), 1356-64).

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compound of formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which modulate the secretion of Aβ (including γ-secretase inhibitors, γ-secretase modulators and β-secretase inhibitors), compounds which inhibit the aggregation of Aβ, and antibodies which selectively bind to Aβ. Such additional compounds further include growth hormone secretagogues, e.g. as described in WO 2004/080459.

In this embodiment of the invention, the amyloid modifier may be a compound which inhibits the secretion of Aβ, for example an inhibitor of γ-secretase (such as those disclosed in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, WO 2004/089911, WO 02/081435, WO 02/081433, WO 03/018543, WO 2004/031137, WO 2004/031139, WO 2004/031138, WO 2004/101538, WO 2004/101539 and WO 02/47671), or a β-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature,* 423 (2003), 435-9.

Alternatively, the amyloid modifier may be a compound which modulates the action of γ-secretase so as to selectively attenuate the production of Aβ(1-42). Compounds reported to show this effect include certain non-steroidal antiinflammatory drugs (NSAIDs) and their analogues (see WO 01/78721 and US 2002/0128319 and Weggen et al *Nature,* 414 (2001) 212-16; Morihara et al, *J. Neurochem.,* 83 (2002), 1009-12; and Takahashi et al, *J. Biol. Chem.,* 278 (2003), 18644-70), and compounds which modulate the activity of PPARα and/or PPARδ (WO 02/100836). Further examples of γ-secretase modulators are disclosed in WO 2005/054193, WO 2005/013985, WO 2005/108362, WO 2006/008558 and WO 2006/043064.

Alternatively, the amyloid modifier may be a compound which inhibits the aggregation of Aβ or otherwise attenuates its neurotoxicicity. Suitable examples include chelating agents such as clioquinol (Gouras and Beal, *Neuron,* 30 (2001), 641-2) and the compounds disclosed in WO 99/16741, in particular that known as DP-109 (Kalendarev et al, *J. Pharm. Biomed. Anal.,* 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 (in particular 3-aminopropane-1-sulfonic acid, also known as tramiprosate or Alzhemed™); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191. Further examples include phytic acid derivatives as disclosed in U.S. Pat. No. 4,847,082 and inositol derivatives as taught in US 2004/0204387.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466. Suitable antibodies also include those specific to Aβ-derived diffusible ligands (ADDLS), as disclosed in WO 2004/031400.

As used herein, the expression "in combination with" requires that therapeutically effective amounts of both the compound of formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of formula I.

The compounds of Formula I disclosed herein are also useful as blood pressure lowering agents and thus useful for the treating hypertension. Arterial hypertension has been identified as a strong causal factor in cardiovascular disease. An embodiment of the invention encompasses a method for treating or preventing cardiovascular disease comprising administering to a patient in need thereof a compound of Formula I, either as a single agent or in combination with other standard of care agents. It is postulated that compounds of the invention lower blood pressure by interfering with binding of tau and other microtubule associated proteins (MAP) to microtubules. Inhibiting the depolymerization of tubulin is the proposed cause of vasorelaxation leading to blood pressure lowering. In unpublished data, several series of MARK inhibitors have demonstrated blood pressure lowering effect in animal models. Example 4 disclosed herein lowered Mean Arterial Pressure by 25% when it was dosed at 5 mg/kg cumulatively over the course of 90 minutes in anesthetized dogs. Example 9 disclosed herein lowered Mean Arterial Pressure by 89% when it was dosed at 10 mg/kg cumulatively over the course of 90 minutes in anesthetized dogs.

Methods of Synthesis

Scheme 1 outlines the general process towards substituted 3-bromo-pyrazolo[1,5-a]pyrimidines. Condensation of 3-amino-4-bromopyrazole 1 with the appropriate substituted iminium hexafluorophosphate or substituted acrolein 2 affords the corresponding 3-bromo-pyrazolo[1,5-a]pyrimidines 3. Treatment of 3 (when X=Br) with potassium hydroxide gives phenol 4 which can be further manipulated into substituted alkoxy pyrazolo[1,5-a]pyrimidines 5.

Cross coupling partners were synthesized following Scheme 2. In case of an ester, methyl 4-bromo-5-ethylthiophene 6 was treated with bispinacolato diboron and Pd(0) affording boronic ester 7. Hydrolysis of the ester with base gives thiophene carboxylic acid boronic ester 8. Similarly 4-bromo-5-ethylthiophene carboxylic acid 9 can be converted to amide 10 via BOP as the coupling reagent. Treatment of amide 10 with bispinacolato diboron and Pd(0) gave substituted amido-thiophene boronic esters 11.

Scheme 3 describes the synthetic route towards enantiomerically pure difluoromethylcyclohexyldiamine 15. Boc-diamine 12 was treated with 13 to afford Fmoc protected diamine 14. Treatment with HCl gave the corresponding HCl salt 15.

The majority of substituted pyrazolo[1,5-a]pyrimidines can be synthesized via Scheme 4. 3-Bromo-pyrazolo[1,5-a]pyrimidine 16 was coupled to thiophene boronic ester 17 to afford coupled product 18 via Suzuki cross coupling. In case of an ester, 18 was hydrolyzed with potassium hydroxide, and amide 20 was formed via the acid chloride or employing BOP as a coupling reagent. Alternatively, if 18 was the carboxylic acid, amide formation was done using BOP as a coupling reagent to give amide 20.

Scheme 5 and Scheme 6 describe other synthetic routes to obtain substituted pyrazolo[1,5-a]pyrimidines. 3-Bromo-5-trifluoromethylpyrazolo[1,5-a]pyrimidine 21 was coupled to thiophene boronic ester 7 giving the methyl ester. Treatment with potassium hydroxide in methanol not only hydrolyzed the ester to the acid, but also gave trimethoxymethyl compound 22. Amide formation was completed using BOP as the coupling reagent followed by BOC deprotection with TFA. Under acidic conditions, the trimethoxymethyl moiety was converted to methyl ester 23. Alternatively, compound 26 was synthesized following Scheme 6. Compound 24 was treated with potassium hydroxide to give phenol 25. Displacement of the triflate group of 2,2,2-trifluoroethyl trifluoromethanesulfonate and deprotection under acidic conditions gave 26.

Scheme 1

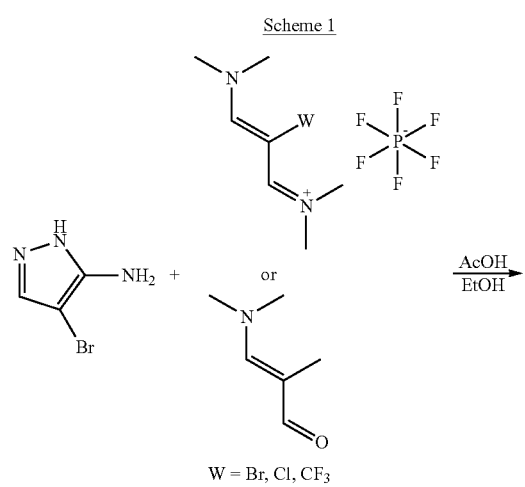

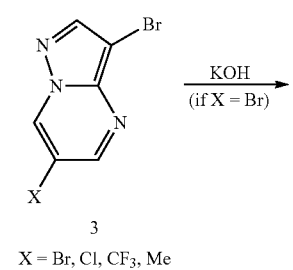

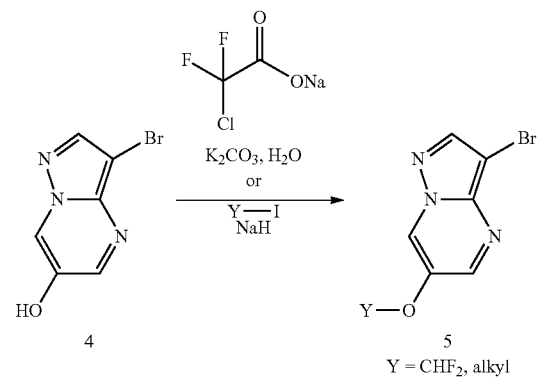

Scheme 2
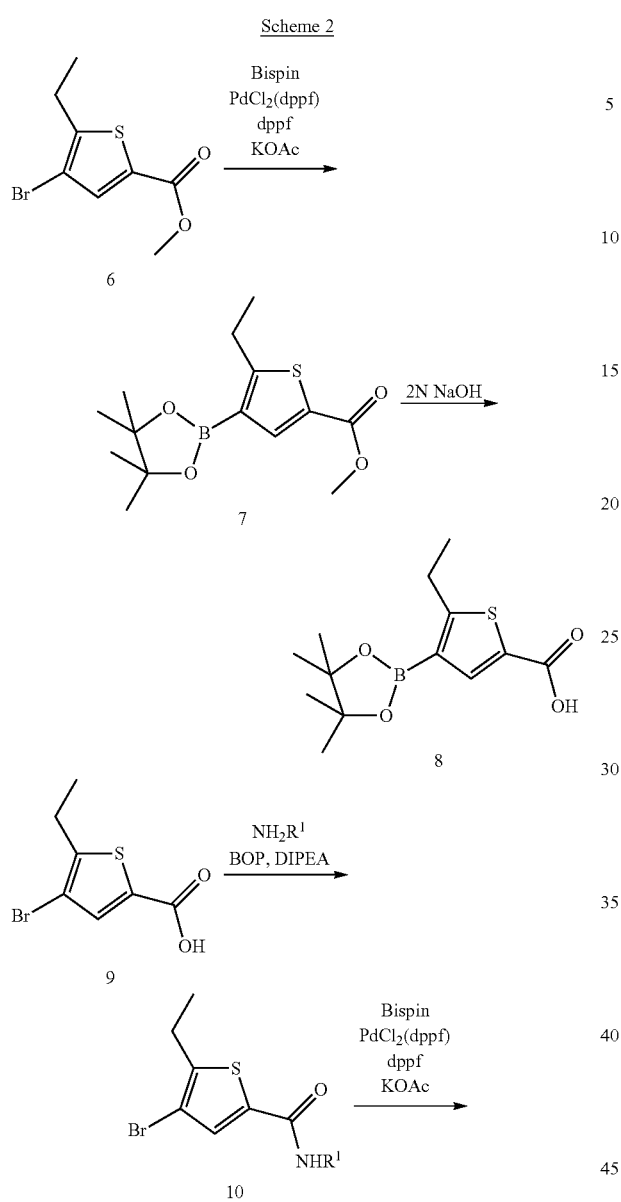
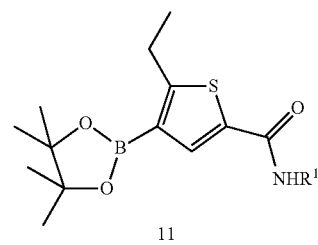
Scheme 3
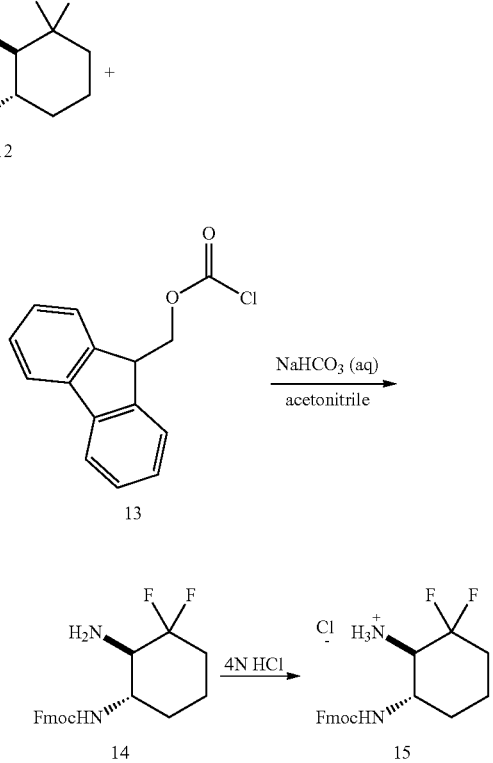
Scheme 4
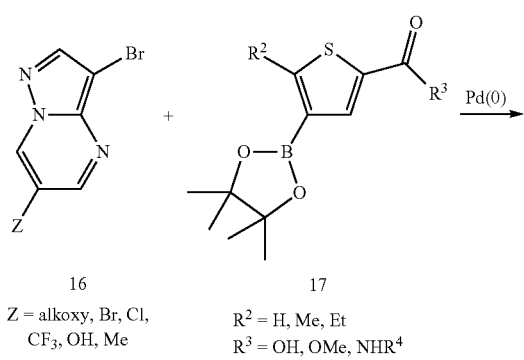
Z = alkoxy, Br, Cl, CF$_3$, OH, Me
R$^2$ = H, Me, Et
R$^3$ = OH, OMe, NHR$^4$

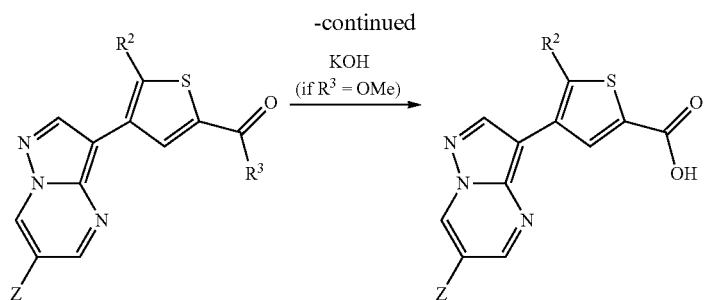
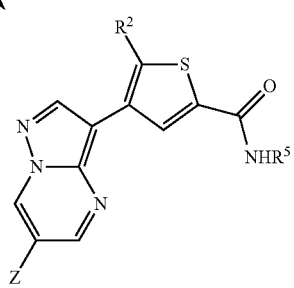
Scheme 5
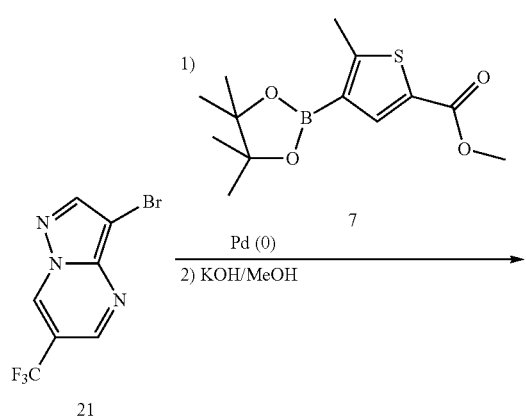
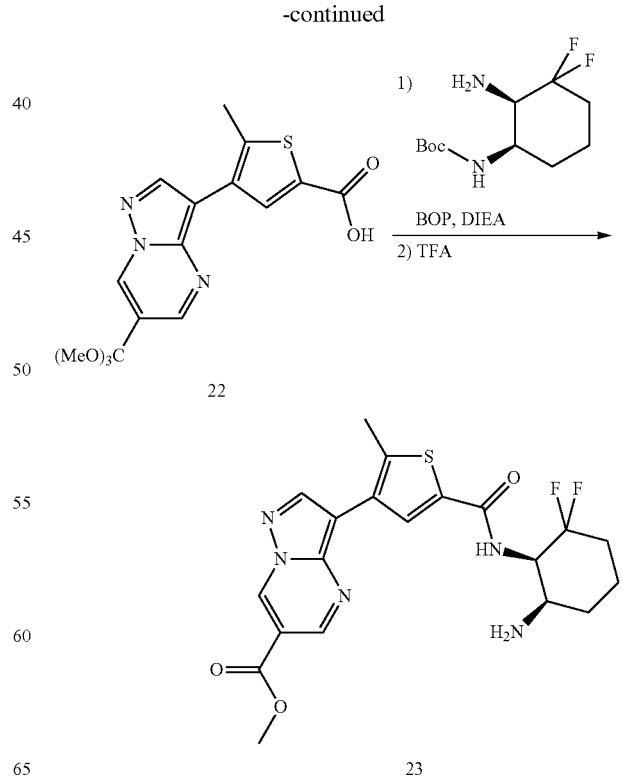

Scheme 6

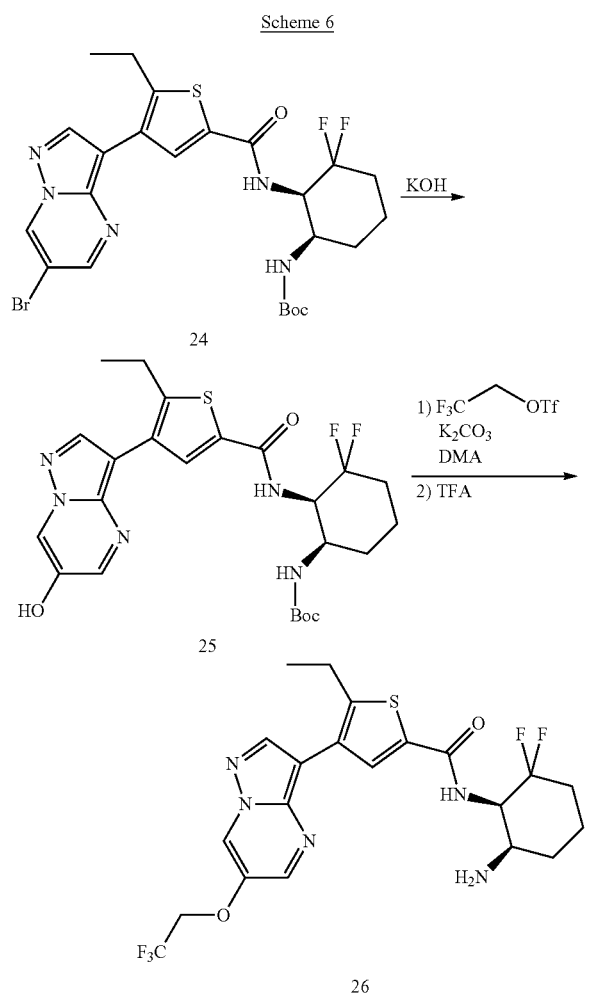

EXAMPLES

Preparation of Substituted 4-Thiophene-Boronic Acid Pinacol Esters

The following methods were used to prepare substituted thiophene boronic esters that were not available from commercial sources or literature.

Method 1

5-Ethyl-4-(4,4,5,5-tetramethyl-1,3,2-dioxaborolan-2-yl)thiophene-2-carboxylic acid

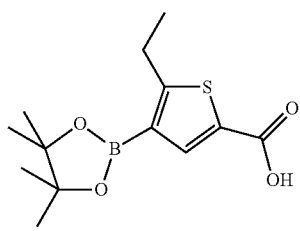 [SMILES: CCc1sc(C(=O)O)cc1B1OC(C)(C)C(C)(C)O1]

Step 1

Methyl-5-ethyl-4-(4,4,5,5-tetramethyl-1,3,2-dioxaborolan-2-yl)thiophene-2-carboxylate

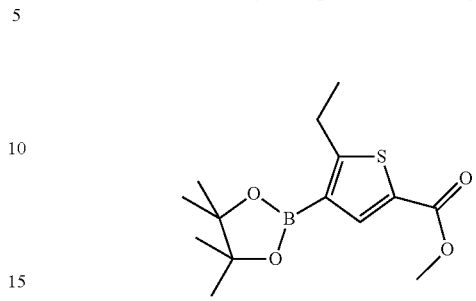

Methyl 4-bromo-5-ethylthiophene-2-carboxylate (1.37 g, 5.50 mmol), bis(pinacolato)diboron (1.54 g, 6.05 mmol), PdCl$_2$(dppf)-CH$_2$Cl$_2$ adduct (0.135 g, 0.165 mmol), dppf (0.091 g, 0.165 mmol), and potassium acetate (1.08 g, 11.0 mmol) were dissolved in 1,4-dioxane (55 mL) and the reaction purged with N$_2$ for 15 min. The reaction was heated at 85° C. for 16 h. The reaction was then cooled to room temperature. Bis(pinacolato)diboron (0.698 g, 2.75 mmol), PdCl$_2$(dppf)-CH$_2$Cl$_2$ adduct (0.135 g, 0.165 mmol), dppf (0.091 g, 0.165 mmol), and potassium acetate (0.540 g, 5.50 mmol) was added and the reaction mixture purged with N$_2$ for 15 min. The reaction was heated at 85° C. for 24 h. Cooled reaction to room temperature, diluted with water and extracted with ethyl acetate 3×. The organic layers were combined, dried with magnesium sulfate, filtered, and concentrated under reduced pressure. The residue was purified by column chromatography (0-40% EtOAc/Hex). The fractions were concentrated under reduced pressure to give the title compound as a blue solid (1.04 g, 3.51 mmol). $^1$H NMR (CDCl$_3$, 500 MHz) δ 7.95 (s, 1H), 3.84 (s, 3H), 3.12 (q, J=7.5, 2H), 1.34 (s, 12H), 1.28 (t, J=7.5, 3H).

Step 2.

5-Ethyl-4-(4,4,5,5-tetramethyl-1,3,2-dioxaborolan-2-yl)thiophene-2-carboxylic acid

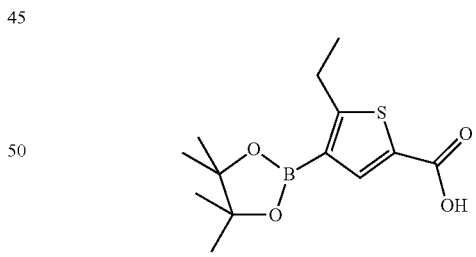

Methyl-5-ethyl-4-(4,4,5,5-tetramethyl-1,3,2-dioxaborolan-2-yl)thiophene-2-carboxylate (2.07 g, 5.05 mmol) was dissolved in methanol (17.7 mL) and 2N NaOH (aq) (17.7 mL, 35.3 mmol). The mixture was stirred at room temperature for 48 h. After hydrolysis was complete, the reaction mixture was concentrated to half volume (to take the methanol off) and then extracted once with diethyl ether (removes excess bis(pinacolato)diboron from previous reaction). The aqueous layer was then acidified with 1N HCl (aq) and extracted 3× with ethyl acetate. The ethyl acetate layers were combined, washed with brine 2×, dried with magnesium sulfate, filtered, and concentrated under reduced pressure. The material was left to dry to give the title compound (quantitative yield). $^1$H NMR (CDCl$_3$, 500 MHz) δ 8.04 (s, 1H), 3.14 (q, J=7.5, 2H), 1.33 (t, J=7.5, 3H), 1.32 (m, 12H).

tert-Butyl[(1R,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate

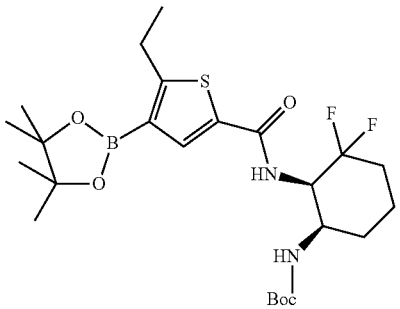 [SMILES: CCc1sc(C(=O)N[C@@H]2[C@H](NC(=O)OC(C)(C)C)CCCC2(F)F)cc1B1OC(C)(C)C(C)(C)O1]

Step 1.

tert-Butyl[(1R,2R)-2-{[(4-bromo-5 ethylthiophen-2-yl)carbonyl]amino}-3,3-difluorocyclohexyl]carbamate

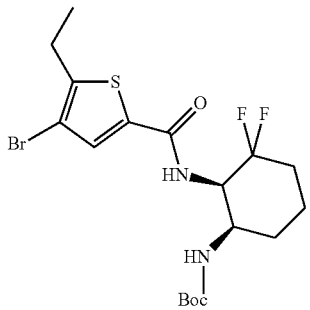 [SMILES: CCc1sc(C(=O)N[C@@H]2[C@H](NC(=O)OC(C)(C)C)CCCC2(F)F)cc1Br]

4-Bromo-5-ethylthiophene-2-carboxylic acid (1.00 g, 4.25 mmol) and BOP (5.64 g, 12.8 mmol) were dissolved in DMF (42.5 mL) and stirred at room temperature for 5 min. To the reaction solution was added tert-butyl [(1R,2R)-2-amino-3,3-difluorocyclohexyl]carbamate (1.07 g, 4.25 mmol) and diisopropylethyl amine (1.11 mL, 6.38 mmol) and the reaction stirred at room temperature for 64 h. The reaction mixture was diluted with ethyl acetate and washed with water 3×. The organic layer was collected, dried with sodium sulfate, filtered, and concentrated under reduced pressure. The residue was purified by column chromatography (0-50% EtOAc/Hex) to give the title compound (1.56 g, 3.34 mmol). LRMS (APCI) calc'd for (C$_{18}$H$_{25}$BrF$_2$N$_2$O$_3$S) [M+H]$^+$, 467.1; found 466.9. $^1$H NMR (CDCl$_3$, 500 MHz) δ 7.32 (s, 1H), 6.28 (s, 1H), 4.90 (s, 1H), 4.54 (s, 1H), 4.29 (s, 1H), 2.81 (q, J=7.5, 2H), 2.22 (m, 1H), 1.88 (m, 1H), 1.81 (m, 1H), 1.69 (m, 1H), 1.59 (m, 1H), 1.46 (s, 9H), 1.41 (m, 1H), 1.28 (t, J=7.3, 3H)

Step 2.

tert-Butyl[(1R,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate

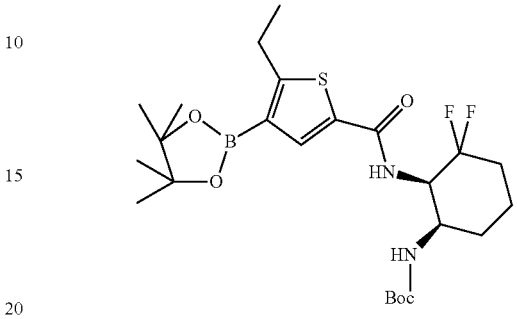

tert-Butyl[(1R,2R)-2-{[(4-bromo-5 ethylthiophen-2-yl)carbonyl]amino}-3,3-difluorocyclohexyl]carbamate (1.50 g, 3.21 mmol), bis(pinacolato)diboron (0.897 g, 3.53 mmol), PdCl$_2$(dppf)-CH$_2$Cl$_2$ adduct (0.157 g, 0.193 mmol), dppf (0.107 g, 0.193 mmol), and potassium acetate (1.26 g, 12.8 mmol) were dissolved in 1,4-dioxane (21.4 mL). The reaction was sealed and purged with argon for 10 min. The reaction was stirred at 85° C. for 16 h. The reaction was then cooled to room temperature. Bis(pinacolato)diboron (0.449 g, 1.77 mmol), PdCl$_2$(dppf)-CH$_2$Cl$_2$ adduct (0.157 g, 0.193 mmol), dppf (0.107 g, 0.193 mmol), and potassium acetate (1.26 g, 12.8 mmol) was added and the reaction mixture purged with argon for 10 min. The reaction was heated at 90° C. for 64 h. The reaction was cooled to room temperature and diluted with water. The aqueous layer was extracted 3× with dichloromethane. The organic layers were combined, dried with sodium sulfate, filtered, and concentrated under reduced pressure. The crude product was purified by column chromatography (20-100% EtOAc/Hex) to give the title compound (1.51 g, 2.94 mmol). LRMS (APCI) calc'd for (C$_{24}$H$_{37}$BF$_2$N$_2$O$_5$S) [M+H]$^+$, 515.3; found 515.0. $^1$H NMR (CDCl$_3$, 500 MHz) δ 7.30 (s, 1H), 6.71 (d, J=8.6, 1H), 5.11 (d, J=8.9, 1H), 4.54 (d, J=22.2, 1H), 4.14 (s, 1H), 2.69 (q, J=7.2, 2H), 2.10 (s, 1H), 1.88-1.55 (m, 5H), 1.37 (s, 12H), 1.29 (s, 9H), 1.17 (t, J=7.4, 3H).

Preparation of Substituted Amines

The following methods were used to prepare substituted amines that were not available from commercial sources or literature.

Method 2

(1R,6S)-6-{[(9H-Fluoren-9-ylmethoxy)carbonyl]amino}-2,2-difluorocyclohexanaminium chloride

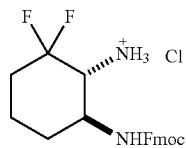

Step 1.

tert-Butyl 9H-fluoren-9-ylmethyl [(1S,2R)-3,3-difluorocyclohexane-1,2-diyl]biscarbamate

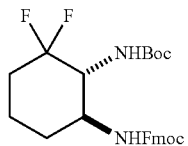

To a slurry of tert-butyl [(1R,6S)-6-amino-2,2-difluorocyclohexyl]carbamate (48.0 g, 192 mmol) and NaHCO$_3$ (32.2 g, 384 mmol) in acetonitrile (500 mL) and water (500 mL) was slowly added FmocCl (54.6 g, 211 mmol) in acetonitrile (300 mL) over 1.5 h. To the slurry was added water (500 mL) and the solid was filtered off and washed with water (250 mL) and hexane (500 mL), then dried under high-vacuum to afford the title compound (quantitative yield). $^1$H NMR (CDCl$_3$, 400 MHz) δ 7.75 (d, 2H); 7.56 (d, 2H); 7.37 (m, 2H); 7.27 (m, 2H); 5.38 (d, 1H); 5.00 (d, 1H); 4.75 (s, 1H); 4.31 (m, 1H); 4.15 (m, 1H); 4.60-4.85 (m, 2H); 1.25-2.20 (series of m, 6H); 1.36 (s, 9H).

Step 2.

(1R,6S)-6-{[(9H-Fluoren-9-ylmethoxy)carbonyl]amino}-2,2-difluorocyclohexanaminium chloride

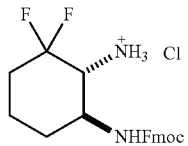

To a slurry of tert-butyl 9H-fluoren-9-ylmethyl [(1S,2R)-3,3-difluorocyclohexane-1,2-diyl]biscarbamate (90 g, 190 mmol) in 1,4-dioxane (500 ml) was added 250 mL of 4N HCl in 1,4-dioxane. The solution was warmed to 50° C. for 2 h. Hexanes (600 mL) was added to the warm slurry over 15 min, then the mixture was cooled to 15° C. The precipitate was filtered, washed with hexanes (400 mL), and dried under high-vacuum to afford the title compound as a white solid (75.0 g, 183 mmol).

Preparation of Substituted Pyrazolopyrimidines

The following methods were used to prepare substituted bromo-pyrazolopyrimidines that were not available from commercial sources or literature.

Method 3

3-Bromo-6-chloropyrazolo[1,5-a]pyrimidine

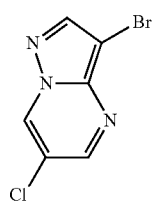

A 5 L 4-neck round bottom flask equipped with mechanical stirrer, thermocouple, condenser and N$_2$ bubbler was charged with 3-amino-4-bromopyrazole (40.0 g, 240 mmol), 2-Chloro-1,3-bis(dimethylamino)trimethinium hexafluorophosphate (77.0 g, 252 mmol) in acetic acid (390 ml)/ethanol (580 ml). The reaction mixture was heated to 70° C. for 8 hrs. Cool to 0° C. Filter off solids. Wash solids with 500 ml water then 500 ml MeOH and dried under high vac to afford the title compound (45.1 g, 194 mmol). LRMS (APCI) calc'd for (C$_6$H$_3$BrClN$_3$) [M+H]$^+$, 231.9; found 231.9. $^1$H NMR (CDCl$_3$, 500 MHz) δ 8.74 (s, 1H), 8.52 (s, 1H), 8.14 (s, 1H).

3-Bromo-6-(trifluoromethyl)pyrazolo[1,5-a]pyrimidine

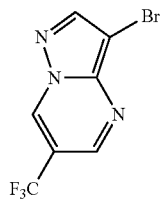

3-Amino-4-bromopyrazole (4.29, 26.5 mmol) and 2-(trifluoromethyl)-1,3-bis(dimethylamino)trimethinium hexafluorophosphate (9.00 g, 26.5 mmol) were dissolved in ethanol (52.9 mL) and acetic acid (35.3 mL) and the reaction heated to 70° C. for 16 h. The solution was cooled to room temperature and concentrated. The residue was filtered through a fritted funnel, the precipitate washed with water, and dried under reduced pressure to afford the title compound (6.22 g, 23.4 mmol). LRMS (APCI) calc'd for (C$_7$H$_3$BrF$_3$N$_3$) [M+H]$^+$, 266.0; found 265.9. $^1$H NMR (CDCl$_3$, 500 MHz) δ 8.96 (d, J=1.1, 2.1, 1H), 8.71 (d, J=2.1, 1H), 8.28 (s, 1H).

3-Bromo-6-methylpyrazolo[1,5-a]pyrimidine

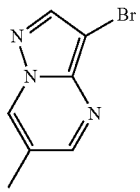

3-Amino-4-bromopyrazole (0.331 g, 2.04 mmol) and 3-(dimethylamino)-2-methyl-2-propenal (0.220 g, 1.94 mmol) were dissolved in acetic acid (6.48 mL) and ethanol (9.72 mL) and the reaction stirred at room temperature for 16 h. Solvents were removed under reduced pressure. The remaining residue was taken up in dichloromethane and purified by column chromatography (20-80% EtOAc/Hex) to give the title compound (0.294 g, 1.39 mmol). LRMS (APCI) calc'd for (C$_7$H$_6$BrN$_3$) [M+H]$^+$, 212.0; found 211.9. $^1$H NMR (500 MHz, cdcl3) δ 8.44 (s, 2H), 8.04 (s, 1H), 2.40 (s, 3H).

3-Bromopyrazolo[1,5-a]pyrimindin-6-ol

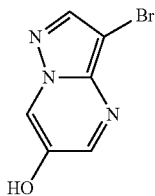

To a flask containing methanol (300 mL) was added 3,6-dibromopyrazolo[1,5-a]pyrimidine (10.0 g, 36.1 mmol) and solid KOH (4.05 g, 72.2 mmol). The reaction was stirred at 65° C. for 64 h. The reaction was cooled to room temperature and the methanol removed under reduced pressure. The crude mixture was taken up in ethyl acetate, washed twice with saturated ammonium chloride (aq), and once with brine. The organic layer was dried over sodium sulfate, filtered, and concentrated under reduced pressure to give the title compound (7.58 g, 35.4 mmol). LRMS (APCI) calc'd for ($C_6H_4BrN_3O$) [M+H]$^+$, 214.0; found 213.9. $^1$H NMR ($CD_3SOCD_3$, 500 MHz,) δ 10.36 (s, 1H), 8.53 (s, 1H), 8.44 (s, 1H), 8.15 (s, 1H).

3-Bromo-6-(difluoromethoxy)pyrazolo[1,5-a]pyrimidine

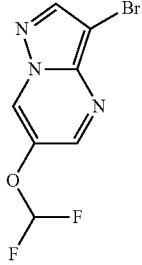 [SMILES: FC(F)Oc1cnc2c(Br)cnn2c1]

Potassium carbonate (1.55 g, 11.2 mmol), sodium chlorodifluoroacetate (2.85 g, 18.7 mmol), and water (2.3 mL) were added to a mixture of 3-bromopyrazolo[1,5-a]pyrimindin-6-ol (2.00 g, 9.34 mmol) and N,N-dimethylacetamide (21.0 mL). The reaction was left to stir at 100° C. for 16 h with appropriate ventilation. The reaction was cooled to room temperature, concentrated, and purified by column chromatography (0-50% EtOAc/Hex) to afford the title compound (1.07 g, 4.06 mmol). LRMS (APCI) calc'd for ($C_7H_4BrF_2N_3O$) [M+H]$^+$, 264.0; found 263.9. $^1$H NMR ($CDCl_3$, 500 MHz) δ 8.64 (s, J=2.3, 1H), 8.51 (s, 1H), 8.15 (s, 1H), 6.60 (t, J=71.3, 1H).

3-Bromo-6-methoxypyrazolo[1,5-a]pyrimidine

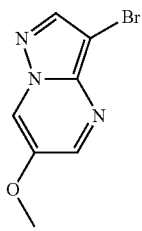

To a flask containing 3-bromopyrazolo[1,5-a]pyrimindin-6-ol (1.28 g, 5.98 mmol) in DMF (15 mL) was added iodomethane (0.411 mL, 6.58 mmol). The reaction was evacuated and filled with argon three times. The mixture was cooled to 0° C. and sodium hydride (0.251 g, 6.28 mmol) added. The reaction was allowed to warm to room temperature and stirred for 2 h. After the reaction is complete, added ethyl acetate and methanol. Washed organic layer with saturated sodium bicarbonate (aq) twice and brine once. The organic layer was dried with sodium sulfate, filtered, and concentrated under reduced pressure. The crude product was purified by column chromatography (0-50% EtOAc/Hex) to give the title compound (0.442 g, 1.94 mmol). LRMS (APCI) calc'd for ($C_7H_6BrN_3O$) [M+H]$^+$, 228.0; found 227.9. $^1$H NMR ($CD_3SOCD_3$, 500 MHz) δ 8.93 (s, 1H), 8.53 (s, 1H), 8.22 (s, 1H), 3.31 (s, 3H).

Example 1

(1R,2R)-2-(([5-Chloro-4-(6-chloropyrazolo[1,5-a]-pyrimindin-3-yl)-thiophen-2-yl]carbonyl)-amino)-3,3-difluorocyclohexanaminium chloride

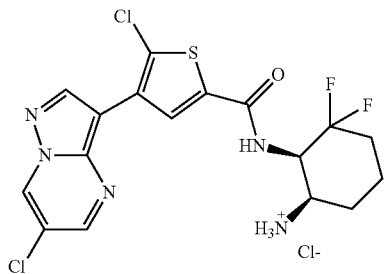

Step 1.

4-(6-Chloropyrazolo[1,5-a]-pyrimidin-3-yl)-thiophene-2-carboxylic acid

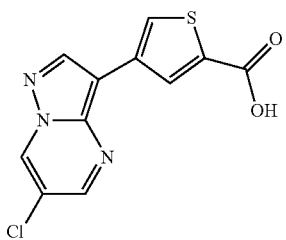 [SMILES: O=C(O)c1cc(-c2cnn3cc(Cl)cnc23)cs1]

To a sealed tube containing DMF (3 mL) and water (1 mL) was added 3-bromo-6-chloropyrazolo[1,5-a]pyrimidine (150 mg, 0.645 mmol), methyl-4-(4,4,5,5,-tetramethyl-1,3,2-dioxaborolan-2-yl)-thiophene-2-carboxylate (216 mg, 0.807 mmol), Biotage polymer-bound triphenylphosphine-Pd(0), and sodium carbonate (85 mg, 0.807 mmol). The reaction flask was backfilled with nitrogen gas three times and irradiated in the microwave at 110° C. for 1 h. The solution was allowed to cool to room temperature, and a 1:1 solution of dichloromethane: methanol was added. The solution was filtered and the resulting filtrate concentrated under reduced pressure and water was added. The precipitate was filtered and washed with water once to afford crude methyl 4-(6- chloropyrazolo[1,5-a]-pyrimindin-3-yl)-thiophene-2-carboxylate. The crude methyl ester was taken up in THF (3 mL) and MeOH (3 mL) and 1N KOH in MeOH (2 mL, 3.10 mmol) was added. The solution was heated at 60° C. for 3 h. After hydrolysis, the solution was acidified with 1N HCl and the precipitate collected by filtration to afford the title compound (0.125 g, 0.447 mmol). LRMS (APCI) calc'd for ($C_{11}H_6ClN_3O_2S$) [M+H]$^+$, 280.0; found 280.0.

Step 2.

(1R,2R)-2-(([5-Chloro-4-(6-chloropyrazolo[1,5-a]-pyrimindin-3-yl)-thiophen-2-yl]carbonyl)-amino)-3,3-difluorocyclohexanaminium chloride

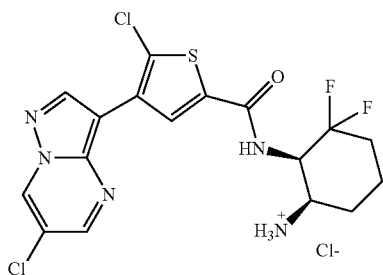 [SMILES: N[C@@H]1CCCC(F)(F)[C@@H]1NC(=O)c1cc(-c2cnn3cc(Cl)cnc23)c(Cl)s1 ; [Cl-]]

To 4-(6-chloropyrazolo[1,5-a]-pyrimidin-3-yl)-thiophene-2-carboxylic acid (50 mg, 0.179 mmol) was added thionyl chloride (2 mL, 27.4 mmol) and the solution heated at 80° C. for 16 h. The solution was then concentrated under reduced pressure and taken up in anhydrous dichloromethane (2 mL). To the solution was added tert-butyl [(1R,2R)-2-amino-3,3-difluorocyclohexyl]carbamate (44.7 mg, 0.179 mmol). The mixture was stirred at room temperature and after consumption of starting material was directly purified by column chromatography (0-50% EtOAc/Hex w/10% DCM and 0.1% NH$_4$OH) to afford the title compound. LRMS (APCI) calc'd for ($C_{17}H_{15}Cl_2F_2N_5OS$) [M+H]$^+$, 446.0; found 446.0. $^1$H NMR (CD$_3$SOCD$_3$, 500 MHz) δ 9.62 (d, J=2.2, 1H), 8.75 (s, 1H), 8.69 (s, 1H), 8.41 (d, J=9.9, 1H), 8.23 (s, 1H), 8.18 (s, 3H), 4.88 (m, 1H), 3.47 (m, 1H), 1.26-1.83 (m, 6H).

Example 2

N-[(1R,6R)-6-Amino-2,2,difluorocyclohexyl]-4-(6-chloropyrazolo[1,5-a]pyrimidin-3-yl)-5-methylthiophene-2-carboxamide

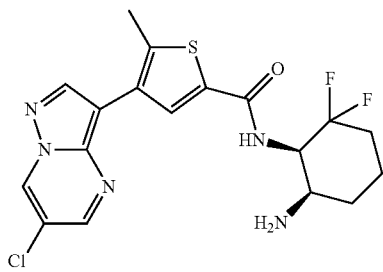 [SMILES: Cc1sc(C(=O)N[C@@H]2[C@H](N)CCCC2(F)F)cc1-c1cnn2cc(Cl)cnc12]

Step 1.

Methyl-4-(6-chloropyrazolo[1,5-a]pyrimidin-3-yl)-5-methylthiophene-2-carboxylate

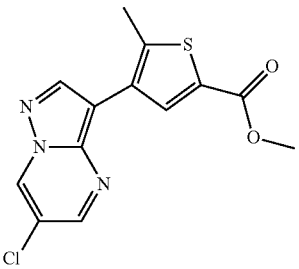 [SMILES: COC(=O)c1cc(-c2cnn3cc(Cl)cnc23)c(C)s1]

To a flask containing 1,4-dioxane (58.1 mL) and water (19.4 mL) was added 3-bromo-6-chloropyrazolo[1,5-a]pyrimidine (3.60 g, 15.5 mmol), methyl-5-methyl-4-(4,4,5,5,-tetramethyl-1,3,2-dioxaborolan-2-yl)-thiophene-2-carboxylate (4.37 g, 15.5 mmol), palladium tetrakis (895 mg, 0.774 mmol), and sodium carbonate (4.92 g, 46.5 mmol). The reaction mixture was sealed and degassed with N$_2$ for 15 min. The reaction mixture was then heated to 100° C. for 2 h. The reaction was cooled to room temperature and partitioned between water and ethyl acetate. The organic layer was dried with sodium sulfate, filtered, and concentrated under reduced pressure. The crude material was purified by column chromatography (dichloromethane:hexane:ethyl acetate 20:75:5 to 20:60:20) to afford the title compound (3.23 g, 10.5 mmol). LRMS (APCI) calc'd for ($C_{13}H_{10}ClN_3O_2S$) [M+H]$^+$, 308.0; found 308.0.

Step 2.

4-(6-Chloropyrazolo[1,5-a]pyrimindin-3-yl)-5-methylthiophene-2-carboxylic acid

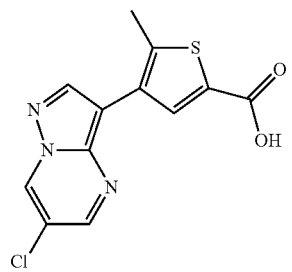 [SMILES: Cc1sc(C(=O)O)cc1-c1cnn2cc(Cl)cnc12]

Methyl-4-(6-chloropyrazolo[1,5-a]pyrimidin-3-yl)-5-methylthiophene-2-carboxylate (2.73 g, 8.87 mmol) was dissolved in methanol (40 mL) and THF (40 mL). 1 M KOH in MeOH (9.31 mL, 9.31 mmol) was added and the reaction heated to 60° C. for 3 h. After the hydrolysis was complete, the reaction was cooled to zero degrees, treated with 1N HCl and the resulting solids were filtered, washed with water and dried to afford the title compound (2.31 g, 7.86 mmol). LRMS (APCI) calc'd for ($C_{12}H_8ClN_3O_2S$) [M+H]$^+$, 294.0; found 294.0.

Step 3.

tert-Butyl-[(1R,2R)-2-({[4-(6-chloropyrazolo[1,5-a]pyrimidin-3-yl)-5-methylthiophen-2-yl]carbonyl}amino)-3,3-difluorocyclohexyl]carbamate

Step 4.

N-[(1R,6R)-6-Amino-2,2,difluorocyclohexyl]-4-(6-chloropyrazolo[1,5-a]pyrimidin-3-yl)-5-methylthiophene-2-carboxamide

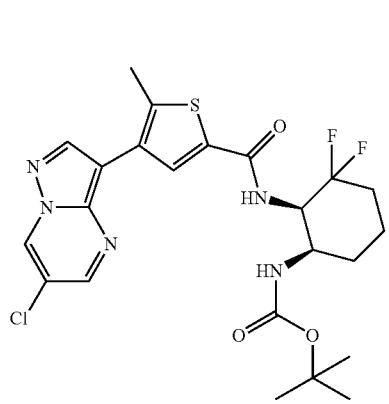 [SMILES: Cc1sc(C(=O)N[C@@H]2[C@H](NC(=O)OC(C)(C)C)CCCC2(F)F)cc1-c1cnn2cc(Cl)cnc12]

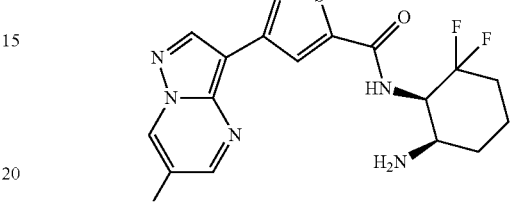

4-(6-Chloropyrazolo[1,5-a]pyrimidin-3-yl)-5-methylthiophene-2-carboxylic acid (2.31 g, 7.86 mmol) was dissolved in thionyl chloride (10 mL, 137 mmol) and heated to 60° C. for 30 min. The reaction was evaporated to dryness under reduced pressure. The acid chloride was then taken up in dichloromethane (10 mL) and then treated with diisopropylethyl amine (2.75 mL, 15.7 mmol) and then tert-butyl [(1R, 2R)-2-amino-3,3-difluorocyclohexyl]carbamate (2.17 g, 8.65 mmol). The resulting reaction was stirred for 30 min at ambient temperature. The reaction was directly dry loaded onto silica and purified by flash chromatography (0-3% MeOH/DCM) to give the title compound (3.36 g, 6.39 mmol). LRMS (APCI) calc'd for ($C_{23}H_{26}ClF_2N_5O_3S$) [M+H]$^+$, 526.1; found 526.0.

To tert-butyl-[(1R,2R)-2-({[4-(6-chloropyrazolo[1,5-a]pyrimidin-3-yl)-5-methylthiophen-2-yl]carbonyl}amino)-3,3-difluorocyclohexyl]carbamate (3.36 g, 6.39 mmol) in dichloromethane (10 mL) was added trifluoroacetic acid (10 mL, 130 mmol) and stirred for 16 h at ambient temperature. The reaction was evaporated to dryness, partitioned dichloromethane and saturated sodium bicarbonate. The aqueous layer was extracted with dichloromethane 3×. The organic layers were combined, dried with sodium sulfate, filtered, and concentrated under reduced pressure to afford the title compound (2.46 g, 5.77 mmol). LRMS (APCI) calc'd for ($C_{18}H_{18}ClF_2N_5OS$) [M+H]$^+$, 426.1; found 426.0. $^1$H NMR (CDCl$_3$, 500 MHz) δ 8.74 (s, 1H), 8.48 (s, 1H), 8.25 (s, 1H), 7.91 (s, 1H), 6.98 (d, J=9.3, 1H), 4.46 (d, J=25.3, 1H), 3.34 (m, 1H), 2.57 (s, 3H), 2.18 (m, 1H), 1.67-1.90 (m, 5H).

According to Example 2, the following compound was prepared from the corresponding amine.

| Compound number | Structure | Name | MS |
|---|---|---|---|
| 3 | 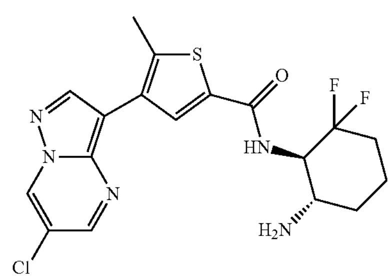 [SMILES: Cc1sc(C(=O)N[C@@H]2[C@@H](N)CCCC2(F)F)cc1-c1cnn2cc(Cl)cnc12] | N-[(1R,6S)-6-amino-2,2-difluorocyclohexyl]-4-(6-chloropyrazolo[1,5-a]pyrimidin-3-yl)-5-methylthiophene-2-carboxamide | calc'd (M + H)$^+$ 425.1; found (M + H)$^+$ 425.0 |

Example 4

N-[(1R,6S)-6-Amino-2,2-difluorocyclohexyl]-4-(6-chloropyrazolo[1,5-a]pyrimindin-3-yl)-5-ethylthiophene-2-carboxamide

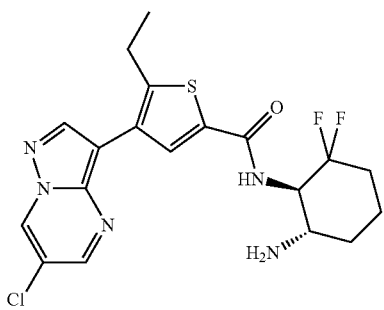 [SMILES: CCc1sc(C(=O)N[C@@H]2[C@@H](N)CCCC2(F)F)cc1-c1cnn2cc(Cl)cnc12]

Step 1.

4-(6-Chloropyrazolo[1,5-a]pyrimindin-3-yl)-5-ethylthiophene-2-carboxylic acid

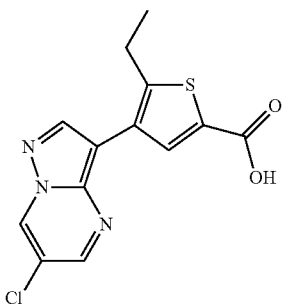 [SMILES: CCc1sc(C(=O)O)cc1-c1cnn2cc(Cl)cnc12]

To 1,4-dioxane (52.4 mL) was added 3-bromo-6-chloropyrazolo[1,5-a]pyrimidine (1.22 g, 5.24 mmol), 5-ethyl-4-(4,4,5,5-tetramethyl-1,3,2-dioxaborolan-2-yl)thiophene-2-carboxylic acid (1.48 g, 5.24 mmol), Pd$_2$(dba)$_3$ (0.479 g, 0.524 mmol), tricyclohexylphosphine (0.367 g, 1.31 mmol), and 3.4M potassium phosphate tribasic (aq) (14.0 mL, 17.8 mmol). The reaction mixture was sealed and purged with N$_2$ for 5 min. The reaction slurry was heated at 100° C. for 1 h. Cooled to room temperature, added 1N HCl, and extracted 3× with 3:1 CHCl$_3$:isopropanol. The organic layers were combined, dried with magnesium sulfate, filtered, and concentrated under reduced pressure. The material was purified by column chromatography (0-100% EtOAc/DCM). The fractions were collected and concentrated under reduced pressure to give the title compound as a yellow solid (1.41 g, 4.58 mmol). LRMS (APCI) calc'd for (C$_{13}$H$_{10}$ClN$_3$O$_2$S) [M+H]$^+$, 308.0; found 307.9.

Step 2.

9H-Fluoren-9-ylmethyl[(1S,2R)-2-({[4-(6-chloropyrazolo[1,5-a]pyrimindin-3-yl)-5-ethylthiophen-2-yl]carbonyl}amino)-3,3-difluorocyclohexyl]carbamate

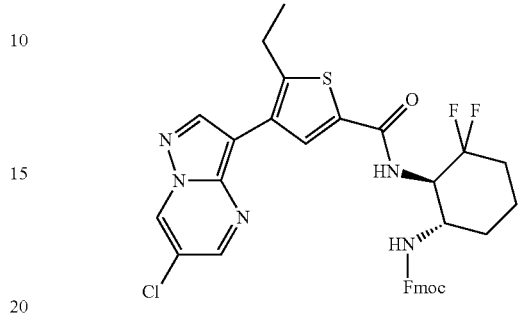

4-(6-Chloropyrazolo[1,5-a]pyrimindin-3-yl)-5-ethylthiophene-2-carboxylic acid (1.73 g, 5.62 mmol) and BOP (2.98 g, 6.75 mmol) were dissolved in DMF (56.2 mL) and stirred at room temperature for 5 min. To the reaction solution was added (1R,6S)-6-{[(9H-fluoren-9-ylmethoxy)carbonyl]amino}-2,2-difluorocyclohexanaminium chloride (2.41 g, 5.90 mmol) and diisopropylethyl amine (3.93 mL, 22.5 mmol) and the reaction stirred at room temperature for 3 h. The reaction was diluted with water and extracted 3× with 3:1 CHCl$_3$:isopropanol. The organic layers were collected, dried with magnesium sulfate, filtered, and concentrated under reduced pressure. The residue was purified by column chromatography (0-100% EtOAc/Hex). The fractions were collected and concentrated to give the title compound as a yellow solid (1.84 g, 2.78 mmol). LRMS (APCI) calc'd for (C$_{34}$H$_{30}$ClF$_2$N$_5$O$_3$S) [M+H]$^+$, 661.1; found 661.0.

Step 3.

N-[(1R,6S)-6-Amino-2,2-difluorocyclohexyl]-4-(6-chloropyrazolo[1,5-a]pyrimindin-3-yl)-5-ethylthiophene-2-carboxamide

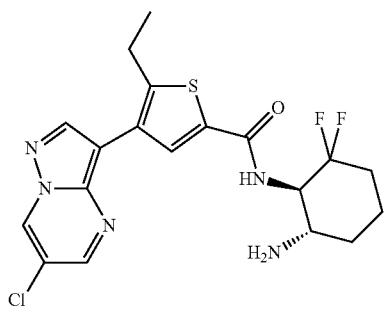 [SMILES: CCc1sc(C(=O)N[C@@H]2[C@@H](N)CCCC2(F)F)cc1-c1cnn2cc(Cl)cnc12]

To 9H-fluoren-9-ylmethyl[(1S,2R)-2-({[4-(6-chloropyrazolo[1,5-a]pyrimindin-3-yl)-5-ethylthiophen-2-yl]carbonyl}amino)-3,3-difluorocyclohexyl]carbamate (1.07 g, 1.62 mmol) in DMF (16.2 mL) was added piperidine (1.60 mL, 16.2 mmol). The mixture was stirred at room temperature for 4 h. After deprotection, water was added and extracted 3× with dichloromethane. The organic layers were combined, dried with magnesium sulfate, filtered, and concentrated under reduced pressure. The material was purified by column chromatography (0-100% EtOAc/Hex, then 0-10% MeOH/DCM). Fractions were collected and concentrated to give the title compound as a yellow solid (0.583 g, 1.33 mmol). LRMS (APCI) calc'd for ($C_{19}H_{20}ClF_2N_5OS$) [M+H]$^+$, 440.1; found 439.9. $^1$H NMR (CD$_3$SOCD$_3$, 500 MHz) δ 9.61 (s, 1H), 8.68 (s, 1H), 8.45 (s, 1H), 8.37 (s, 1H), 8.15 (s, 1H), 4.02 (m, 1H), 2.93 (q, J=7.7, 2H), 2.81 (m, 1H), 2.05 (m, 1H), 1.84 (m, 2H), 1.25-1.85 (m, 3H), 1.22 (t, J=6.9, 3H).

According to Example 4, the following compound was prepared from the corresponding amine.

dioxaborolan-2-yl)thiophene-2-carboxylic acid (199 mg, 0.620 mmol), Pd$_2$(dba)$_3$ (56.8 mg, 0.062 mmol), tricyclohexylphosphine (43.5 mg, 0.155 mmol), and 1.27 M potassium phosphate tribasic (aq) (1.65 mL, 2.10 mmol) were placed in a sealed tube and purged with N$_2$ for 5 min. The reaction was heated to 100° C. for 2 h. The reaction was then cooled to room temperature, diluted with water, and extracted with ethyl acetate 3×. The organic layers were combined, washed with brine, dried with sodium sulfate, filtered, and concentrated under reduced pressure. The residue was purified by column chromatography (10-60% DCM/EtOAc). The

| Compound number | Structure | Name | MS |
|---|---|---|---|
| 5 | 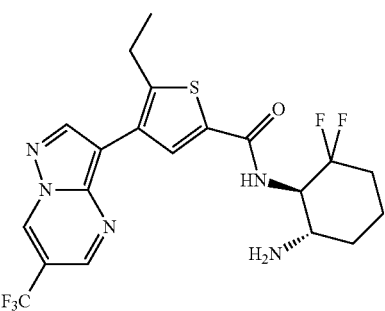 | N-[(1R,6R)-6-amino-2,2-difluorocyclohexyl]-4-(6-chloropyrazolo[1,5-a]pyrimidin-3-yl)-5-ethylthiophene-2-carboxamide | calc'd (M + H)$^+$ 440.1; found (M + H)$^+$ 440.0 |

Example 6

N-[(1R,6S)-6-Amino-2,2-difluorocyclohexyl]-5-ethyl-4-[6-(trifluoromethyl)pyrazolo[1,5-a]pyrimidin-3-yl]thiophene-2-carboxamide

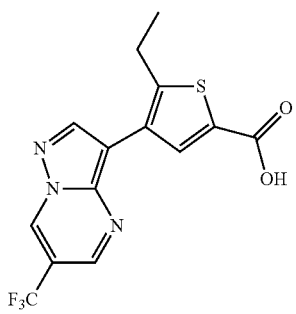 [SMILES: CCc1sc(C(=O)O)cc1-c1cnn2cc(C(F)(F)F)cnc12]

Step 1.

5-Ethyl-4-[6-(trifluoromethyl)pyrazolo[1,5-a]pyrimidin-3-yl]thiophene-2-carboxylic acid

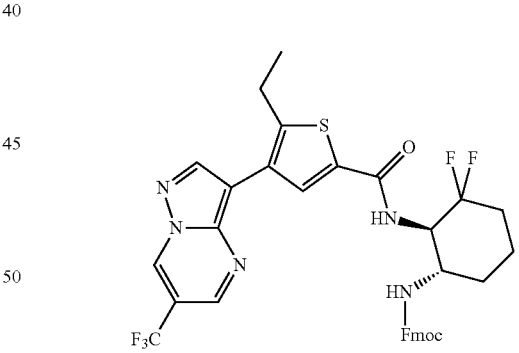

3-Bromo-6-(trifluoromethyl)pyrazolo[1,5-a]pyrimidine (165 mg, 0.620 mmol), 5-ethyl-4-(4,4,5,5-tetramethyl-1,3,2- fractions were combined and concentrated to give the title compound (95.0 mg, 0.278 mmol). LRMS (APCI) calc'd for ($C_{14}H_{10}F_3N_3O_2S$) [M+H]$^+$, 342.0; found 341.9.

Step 2.

9H-Fluoren-9-ylmethyl{(1S,2R)-2-[({5-ethyl-4-[6-(trifluoromethyl)pyrazolo[1,5-a]pyrimidin-3-yl]thiophen-2-yl}carbonyl)amino]-3,3-difluorocyclhexyl)carbamate 5-Ethyl-4-[6-(trifluoromethyl)pyrazolo[1,5-a]pyrimidin-3-yl]thiophene-2-carboxylic acid (47.0 mg, 0.138 mmol) and BOP (73.1 mg, 0.165 mmol) were dissolved in DMF (1.0 mL) and stirred at room temperature for 5 min. To the reaction solution was added (1R,6S)-6-{[(9H-fluoren-9-ylmethoxy)carbonyl]amino}-2,2-difluorocyclohexanaminium chloride (61.9 mg, 0.151 mmol) and diisopropylethyl amine (72.2 μL, 0.413 mmol) and the reaction stirred at room temperature for 2 h. The mixture was then concentrated under reduced pressure and purified by column chromatography (0-50% EtOAc/DCM) to give the title compound (43.0 mg, 0.062 mmol). LRMS (APCI) calc'd for ($C_{35}H_{30}F_5N_5O_3S$) [M+H]$^+$, 696.2; found 696.2.

Step 3.

N-[(1R,6S)-6-Amino-2,2-difluorocyclohexyl]-5-ethyl-4-(6-(trifluoromethyl)pyrazolo[1,5-a]pyrimidin-3-yl)thiophene-2-carboxamide

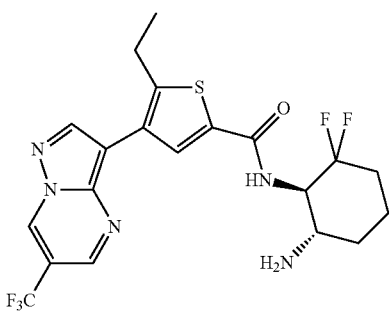 [SMILES: CCc1sc(C(=O)N[C@@H]2[C@@H](N)CCCC2(F)F)cc1-c1cnn2cc(C(F)(F)F)cnc12]

9H-Fluoren-9-ylmethyl{(1S,2R)-2-[({5-ethyl-4-[6-(trifluoromethyl)pyrazolo[1,5-a]pyrimidin-3-yl]thiophen-2-yl}carbonyl)amino]-3,3-difluorocyclhexyl}carbamate (43.0 mg, 0.062 mmol) was dissolved in DMF (618 μL) and piperidine (122 μL, 1.24 mmol) was added to the reaction mixture. The reaction was stirred for 1 h at room temperature, concentrated under reduced pressure, and purified by column chromatography (0-15% MeOH/DCM). The fractions were collected and concentrated to give the title compound (5 mg, 10.6 μmol). LRMS (APCI) calc'd for ($C_{20}H_{20}F_5N_5OS$) [M+H]$^+$, 474.1; found 474.0. $^1$H NMR (CDCl$_3$, 500 MHz) δ 9.01 (s, 1H), 8.69 (s, 1H), 8.39 (s, 1H), 7.91 (s, 1H), 6.20 (d, J=9.4, 1H), 4.21 (m, 1H), 3.00 (q, J=7.5, 2H), 2.77 (m, 1H), 2.24 (m, 1H), 1.46-1.92 (m, 5H), 1.36 (t, J=7.5, 3H).

According to Example 6, the following compound was prepared from the corresponding amine.

Example 8

Methyl-3-(5-{[(1R,6R)-6-amino-2,2-difluorocyclohexyl]carbamoyl}-2-methylthiophen-3-yl)pyrazolo[1,5-a]pyrimidine-6-carboxylate

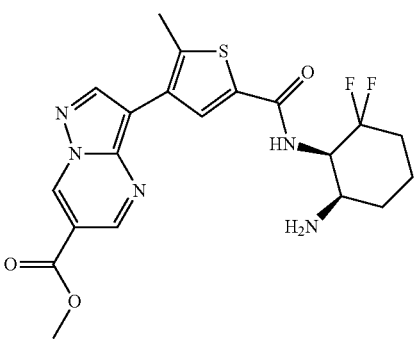 [SMILES: COC(=O)c1cnc2c(-c3cc(C(=O)N[C@@H]4[C@H](N)CCCC4(F)F)sc3C)cnn2c1]

Step 1.

Methyl-5-methyl-4-[6-(trifluoromethyl)pyrazolo[1,5-a]pyrimidin-3-yl]thiophene-2-carboxylate

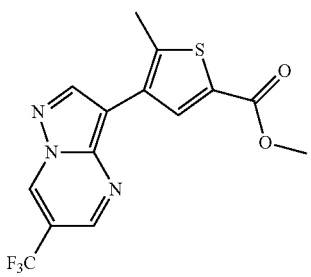 [SMILES: COC(=O)c1cc(-c2cnn3cc(C(F)(F)F)cnc23)c(C)s1]

3-Bromo-6-(trifluoromethyl)pyrazolo[1,5-a]pyrimidine (200 mg, 0.752 mmol), methyl-5-methyl-4-(4,4,5,5,-tetramethyl-1,3,2-dioxaborolan-2-yl)-thiophene-2-carboxylate

| Compound number | Structure | Name | MS |
|---|---|---|---|
| 7 | 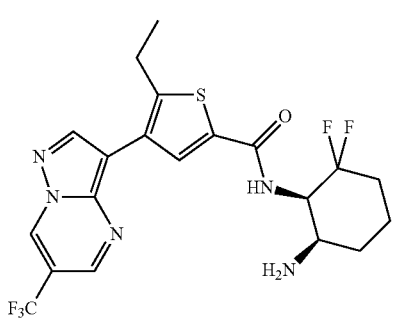 | N-[(1R,6R)-6-amino-2,2-difluorocyclohexyl]-5-ethyl-4-(6-(trifluoromethyl)pyrazolo[1,5-a]pyrimidin-3-yl)thiophene-2-carboxamide | calc'd (M + H)$^+$ 440.1; found (M + H)$^+$ 440.0 |

(297 mg, 1.05 mmol), Pd(PPh$_3$)$_4$ (43.4 mg, 0.038 mmol), and 2 M sodium carbonate (aq) (750 μL, 1.50 mmol) were placed in a sealed tube. 1,4-dioxane (3.75 mL) was added and the reaction purged with N$_2$ for 5 min. The reaction was heated to 85° C. for 7 h. After consumption of starting material, the reaction was cooled to room temperature, diluted with water and extracted 3× with ethyl acetate. The organic layers were combined, washed with brine, dried with sodium sulfate, filtered, and concentrated under reduced pressure. The residue was purified by column chromatography (0-70% EtOAc/Hex) to afford the title compound (120 mg, 0.352 mmol). LRMS (APCI) calc'd for (C$_{14}$H$_{10}$F$_3$N$_3$O$_2$S) [M+H]$^+$, 342.0; found 342.0.
Step 2.

5-Methyl-4-[6-(trimethoxymethyl)pyrazolo[1,5-a]pyrimidin-3-yl]thiophene-2-carboxylic acid

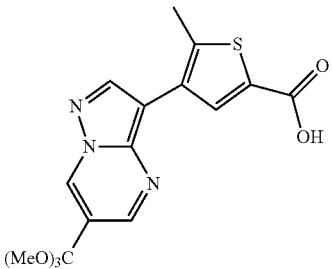

Methyl-5-methyl-4-[6-(trifluoromethyl)pyrazolo[1,5-a]pyrimidin-3-yl]thiophene-2-carboxylate (120 mg, 0.352 mmol) was dissolved in methanol (2 mL) and THF (2 mL). 1M in KOH (1.06 mL, 1.06 mmol) was added and the reaction heated to 60° C. for 2 h. After the hydrolysis was complete, the reaction was treated with 1N HCl, extracted 3× with 3:1 CHCl$_3$:isopropanol. The organic layers were combined, dried with sodium sulfate, filtered, and concentrated under reduced pressure. The material was purified by column chromatography (50-100% EtOAc/DCM) to afford the title compound (83 mg, 0.228 mmol). LRMS (APCI) calc'd for (C$_{16}$H$_{17}$N$_3$O$_5$S) [M+H]$^+$, 364.1; found 364.1.
Step 3.

tert-Butyl{(1R,2R)-3,3-difluoro-2-[({5-methyl-4-[6-(trimethoxymethyl)pyrazolo[1,5-a]pyrimidin-3-yl]thiophen-2-yl}carbonyl)amino]cyclohexyl}carbamate

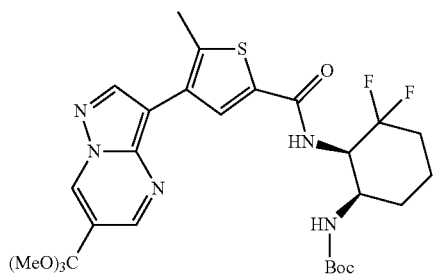

5-Methyl-4-[6-(trimethoxymethyl)pyrazolo [1,5-a]pyrimidin-3-yl]thiophene-2-carboxylic acid (41.0 mg, 0.113 mmol) and BOP (59.9 mg, 0.135 mmol) were dissolved in DMF (752 μL) and stirred at room temperature for 5 min. To the reaction solution was added tert-butyl [(1R,2R)-2-amino-3,3-difluorocyclohexyl]carbamate (31.1 mg, 0.124 mmol) and diisopropylethyl amine (59.1 μL, 0.338 mmol) and the reaction stirred at room temperature for 2 h. The reaction was then concentrated under reduced pressure and purified by column chromatography (0-60% EtOAc/DCM) to afford the title compound (quantitative yield). LRMS (APCI) calc'd for (C$_{27}$H$_{35}$F$_2$N$_5$O$_6$S) [M+H]$^+$, 596.2; found 596.1.
Step 4.

Methyl-3-(5-{[(1R,6R)-6-amino-2,2-difluorocyclohexyl]carbamoyl}-2-methylthiophen-3-yl)pyrazolo[1,5-a]pyrimidine-6-carboxylate

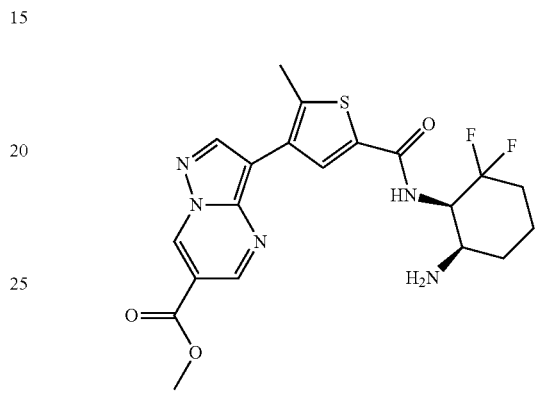

tert-Butyl{(1R,2R)-3,3-difluoro-2-[({5-methyl-4-[6-(trimethoxymethyl)pyrazolo[1,5-a]pyrimidin-3-yl]thiophen-2-yl}carbonyl)amino]cyclohexyl}carbamate (45 mg, 0.076 mmol) was dissolved in dichloromethane (2 mL) and trifluoroacetic acid (275 μL, 3.55 mmol) added. The reaction mixture was stirred at room temperature for 1 h, neutralized with saturated sodium bicarbonate (aq) and extracted 3× with dichloromethane. The organic layers were combined and dried with sodium sulfate, concentrated and purified by column chromatography (0-10% MeOH/DCM) to afford the title compound (quantitative yield). LRMS (APCI) calc'd for (C$_{20}$H$_{21}$F$_2$N$_5$O$_3$S) [M+H]$^+$, 450.1; found 450.1. $^1$H NMR (CDCl$_3$, 500 MHz) δ 9.33 (s, 1H), 9.03 (s, 1H), 8.40 (s, 1H), 7.93 (s, 1H), 6.98 (d, J=8.1, 1H), 4.45 (d, J=25.3, 1H), 4.01 (s, 3H), 3.34 (s, 1H), 2.60 (s, 3H), 2.18 (s, 1H), 1.70-1.90 (s, 5H).

Example 9

N-[(1R,6R)-6-Amino-2,2-difluorocyclohexyl]-4-[6-(difluoromethoxy)pyrazolo[1,5-a]pyrimidin-3-yl]-5-methylthiophene-2-carboxamide

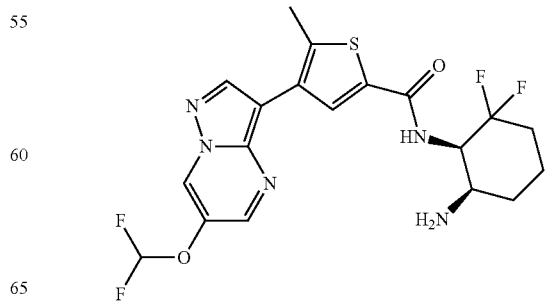

Step 1.

Methyl-4-[6-(difluoromethoxy)pyrazolo[1,5-a]pyrimidin-3-yl]-5-methylthiophene-2-carboxylate

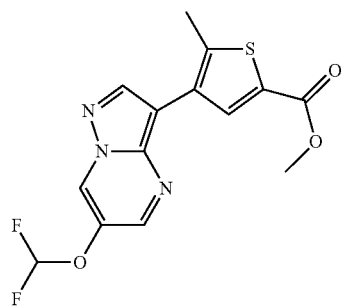 [SMILES: COC(=O)c1cc(-c2cnn3cc(OC(F)F)cnc23)c(C)s1]

To a flask containing DMF (40.6 mL) was added 3-bromo-6-(difluoromethoxy)pyrazolo[1,5-a]pyrimidine (1.07 g, 4.06 mmol), methyl-5-methyl-4-(4,4,5,5,-tetramethyl-1,3,2-dioxaborolan-2-yl)-thiophene-2-carboxylate (1.20 g, 4.27 mmol), palladium tetrakis (235 mg, 0.203 mmol), and 2 M sodium carbonate (aq) (6.10 mL, 12.2 mmol). The reaction mixture was sealed and degassed with $N_2$ for 5 min. The reaction mixture was then heated to 85° C. for 16 h. The reaction mixture was cooled to room temperature and diluted with dichloromethane. The organic layer was washed twice with saturated sodium bicarbonate (aq) twice and once with brine. The organic layer was dried with sodium sulfate, filtered, and concentrated under reduced pressure. The residue was purified by column chromatography (0-80% EtOAc/Hex) to afford the title compound (0.916 g, 2.70 mmol). LRMS (APCI) calc'd for ($C_{14}H_{11}F_2N_3O_3S$) [M+H]$^+$, 340.1; found 340.0.

Step 2.

4-[6-(Difluoromethoxy)pyrazolo[1,5-a]pyrimidin-3-yl]-5-methylthiophene-2-carboxylic acid

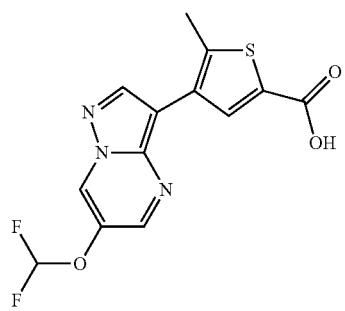 [SMILES: Cc1sc(C(=O)O)cc1-c1cnn2cc(OC(F)F)cnc12]

Methyl-4-[6-(difluoromethoxy)pyrazolo[1,5-a]pyrimidin-3-yl]-5-methylthiophene-2-carboxylate (0.916 g, 2.70 mmol) was dissolved in THF (4 mL). 1 M KOH in MeOH (12.0 mL, 12.0 mmol) was added and the reaction heated to 40° C. for 16 h. After the hydrolysis was complete, treated with 1N HCl and the resulting solids were filtered, washed with water and dried to afford the title compound (0.568 g, 1.75 mmol). LRMS (APCI) calc'd for ($C_{13}H_9F_2N_3O_3S$) [M+H]$^+$, 326.0; found 326.0.

Step 3.

tert-Butyl{(1R,2R)-2-[({4-[6-(difluoromethoxy)pyrazolo[1,5-a]pyrimidin-3-yl]-5-methylthiophen-2-yl}carbonyl)amino]-3,3-difluorocyclohexyl}carbamate

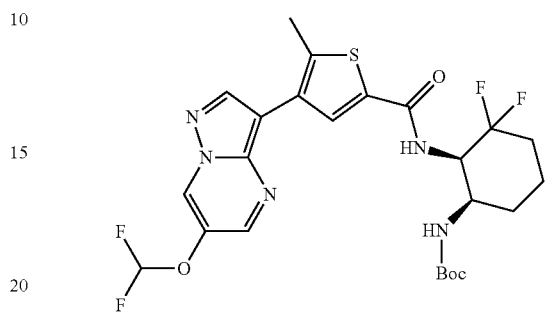

4-[6-(Difluoromethoxy)pyrazolo[1,5-a]pyrimidin-3-yl]-5-methylthiophene-2-carboxylic acid (0.768 g, 2.36 mmol) and BOP (3.13 g, 7.08 mmol) were dissolved in DMF (15.7 mL) and stirred at room temperature for 5 min. To the reaction solution was added tert-butyl [(1R,2R)-2-amino-3,3-difluorocyclohexyl]carbamate (0.650 g, 2.60 mmol) and diisopropylethyl amine (619, 3.54 mmol) and the reaction stirred at room temperature for 16 h. The reaction mixture was diluted with dichloromethane and washed with saturated sodium bicarbonate twice and brine once. The organic layer was dried with sodium sulfate, filtered, and concentrated under reduced pressure. The residue was purified by column chromatography (0-100% EtOAc/Hex) to give the title compound (0.900 g, 1.61 mmol). LRMS (APCI) calc'd for ($C_{24}H_{27}F_4N_5O_4S$) [M+H]$^+$, 558.2; found 558.0.

Step 4.

N-[(1R,6R)-6-Amino-2,2-difluorocyclohexyl]-4-[6-(difluoromethoxy)pyrazolo[1,5-a]pyrimidin-3-yl]-5-methylthiophene-2-carboxamide

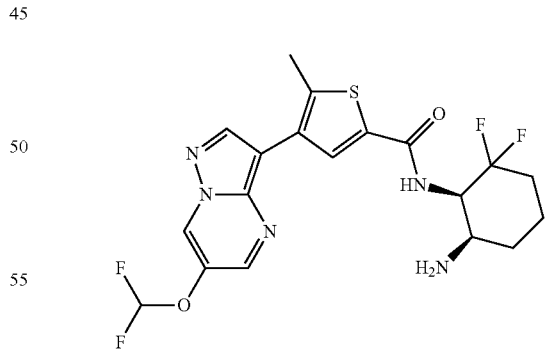

tert-Butyl{(1R,2R)-2-[({4-[6-(difluoromethoxy)pyrazolo[1,5-a]pyrimidin-3-yl]-5-methylthiophen-2-yl}carbonyl)amino]-3,3-difluorocyclohexyl}carbamate (0.900 g, 1.61 mmol) was dissolved in dichloromethane (8 mL) and trifluoroacetic acid (1.50 mL, 19.5 mmol) added. The reaction was stirred at room temperature for 16 h. After deprotection was complete, the mixture was diluted with 1N NaOH. The aqueous layer was extracted 3× with dichloromethane. The organic layers were combined, dried with sodium sulfate, and concentrated under reduced pressure. The residue was purified by column chromatography (0-16% MeOH/DCM) to give the title compound (0.371 g, 0.811 mmol). LRMS (APCI) calc'd for ($C_{19}H_{19}F_4N_5O_2S$) [M+H]$^+$, 458.1; found 458.0. $^1$H NMR (CDCl$_3$, 500 MHz) δ 8.66 (d, J=2.5, 1H), 8.48 (d, J=2.5, 1H), 8.26 (s, 1H), 7.92 (s, 1H), 7.06 (d, J=8.8, 1H), 6.61 (t, J=71.5, 1H), 4.45 (m, 1H), 3.32 (m, 1H), 2.57 (s, 3H), 2.17 (m, J=8.6, 1H), 1.47-1.92 (m, 5H).

According to Example 9, the following compound was prepared from the corresponding alkoxypyrazolopyrimidine and amine.

| Compound number | Structure | Name | MS |
|---|---|---|---|
| 10 | 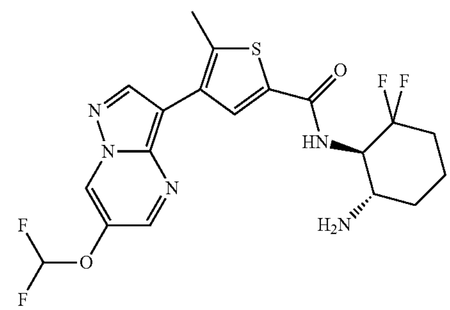 [SMILES: Cc1sc(C(=O)N[C@@H]2[C@@H](N)CCCC2(F)F)cc1-c1cnn2cc(OC(F)F)cnc12] | N-[(1R,6S)-6-amino-2,2-difluorocyclohexyl]-4-[6-(difluoromethoxy)pyrazolo[1,5-a]pyrimidin-3-yl]-5-methylthiophene-2-carboxamide | calc'd (M + H)$^+$ 458.1; found (M + H)$^+$ 458.0 |
| 11 | 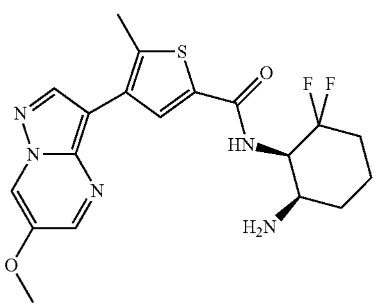 [SMILES: COc1cnc2c(-c3cc(C(=O)N[C@@H]4[C@H](N)CCCC4(F)F)sc3C)cnn2c1] | N-[(1R,6R)-6-amino-2,2-difluorocyclohexyl]-4-[6-methoxypyrazolo[1,5-a]pyrimidin-3-yl]-5-methylthiophene-2-carboxamide | calc'd (M + H)$^+$ 422.1; found (M + H)$^+$ 422.1 |
| 12 | 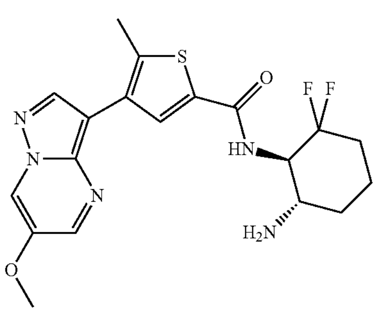 [SMILES: COc1cnc2c(-c3cc(C(=O)N[C@@H]4[C@@H](N)CCCC4(F)F)sc3C)cnn2c1] | N-[(1R,6S)-6-amino-2,2-difluorocyclohexyl]-4-[6-methoxypyrazolo[1,5-a]pyrimidin-3-yl]-5-methylthiophene-2-carboxamide | calc'd (M + H)$^+$ 422.1; found (M + H)$^+$ 422.1 |

Example 13

N-[(1R,6R)-6-Amino-2,2-difluorocyclohexyl]-4-[6-(difluoromethoxy)pyrazolo[1,5-a]pyrimidin-3-yl]-5-ethylthiophene-2-carboxamide

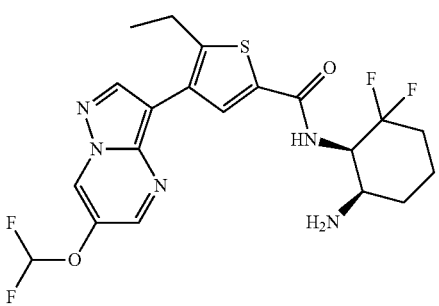 [SMILES: CCc1sc(C(=O)N[C@@H]2[C@H](N)CCCC2(F)F)cc1-c1cnn2cc(OC(F)F)cnc12]

Step 1.

tert-Butyl{(1R,2R)-2-[({4-[6-(difluoromethoxy)pyrazolo[1,5-a]pyrimidin-3-yl]-5-ethylthiophen-2-yl}carbonyl)amino]-3,3-difluorocyclohexyl}carbamate

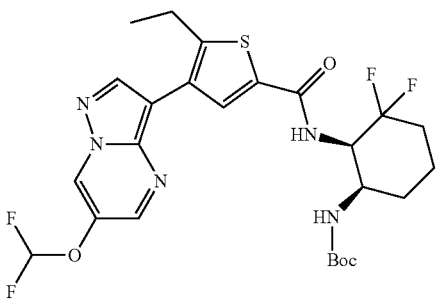 [SMILES: CCc1sc(C(=O)N[C@@H]2[C@H](NC(=O)OC(C)(C)C)CCCC2(F)F)cc1-c1cnn2cc(OC(F)F)cnc12]

3-Bromo-6-(difluoromethoxy)pyrazolo[1,5-a]pyrimidine (0.030 g, 0.114 mmol), tert-butyl[(1R,2R)-2-({[5-ethyl-4-(4,4,5,5-tetramethyl-1,3,2-dioxaborolan-2-yl)thiophen-2-yl]carbonyl}amino)-3,3-difluorocyclohexyl]carbamate (0.059 g, 0.115 mmol), Pd(PPh$_3$)$_4$ (6.57 mg, 0.007 mmol), and 2 M Na$_2$CO$_3$ (aq) (0.170 mL, 0.341 mmol) were placed in a sealed tube and DMF (1.14 mL) added. The mixture was purged with N$_2$ for 5 min. The reaction was heated to 85° C. for 16 h. The mixture was cooled to room temperature, diluted with dichloromethane, and washed twice with saturated sodium bicarbonate (aq) and once with brine. The organic layer was dried with sodium sulfate, filtered, and concentrated under reduced pressure. The crude product was purified by column chromatography (0-70% EtOAc/Hex) to give the title compound (0.037 g, 0.064 mmol). LRMS (APCI) calc'd for (C$_{25}$H$_{29}$F$_4$N$_5$O$_4$S) [M+H]$^+$, 572.2; found 572.1.

Step 2.

N-[(1R,6R)-6-Amino-2,2-difluorocyclohexyl]-4-[6-(difluoromethoxy)pyrazolo[1,5-a]pyrimidin-3-yl]-5-ethylthiophene-2-carboxamide

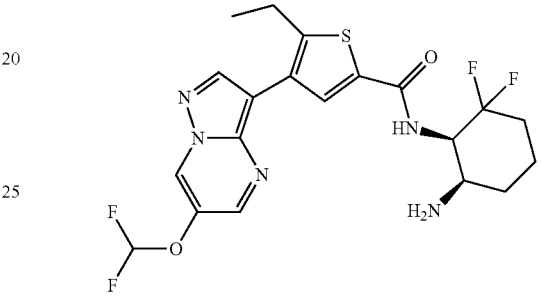

tert-Butyl {(1R,2R)-2-[({4-[6-(difluoromethoxy)pyrazolo[1,5-a]pyrimidin-3-yl]-5-ethylthiophen-2-yl}carbonyl)amino]-3,3-difluorocyclohexyl}carbamate (0.037 g, 0.064 mmol) was dissolved in dichloromethane (0.639 mL) and trifluoroacetic acid (0.250 mL, 3.24 mmol) was added. The reaction was stirred at room temperature for 2 h. 5N NaOH (aq) was added and extracted 3× with dichloromethane. The organic layers were combined, dried with sodium sulfate, filtered, and concentrated. The material was purified by column chromatography (0-5% MeOH/DCM) to give the title compound. LRMS (APCI) calc'd for (C$_{20}$H$_{21}$F$_4$N$_5$O$_2$S) [M+H]$^+$, 472.1; found 472.1. $^1$H NMR (CD$_3$OD, 500 MHz) δ 9.04 (d, J=2.4, 1H), 8.59 (d, J=2.4, 1H), 8.35 (s, 1H), 8.13 (s, 1H), 6.97 (t, J=72.5, 1H), 3.24 (s, 1H), 3.02 (q, J=7.5, 2H), 2.15 (s, 1H), 1.48-1.99 (m, 4H), 1.32 (t, 3H), 1.00-1.18 (m, 2H).

According to Example 13, the following compound was prepared from the corresponding pyrazolopyrimidine and amine.

| Compound number | Structure | Name | MS |
| --- | --- | --- | --- |
| 14 | ![structure] | N-[(1R,6S)-6-amino-2,2-difluorocyclohexyl]-6-ethyl-4-(6-methoxypyrazolo[1,5-a]pyrimidin-3-yl)thiophene-2-carboxamide | calc'd (M + H)$^+$ 436.2; found (M + H)$^+$ 436.1 |

-continued

| Compound number | Structure | Name | MS |
|---|---|---|---|
| 15 | 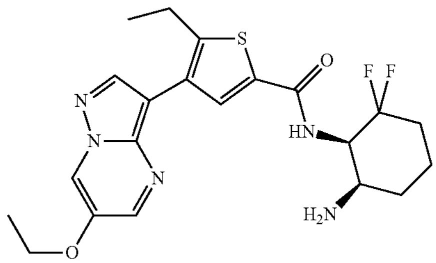 [SMILES: CCOc1cnc2c(-c3cc(C(=O)N[C@@H]4[C@H](N)CCCC4(F)F)sc3CC)cnn2c1] | N-[(1R,6R)-6-amino-2,2-difluorocyclohexyl]-4-(6-ethoxypyrazolo[1,5-a]pyrimidin-3-yl)-5-ethylthiophene-2-carboxamide | calc'd (M + H)$^+$ 450.2; found (M + H)$^+$ 450.1 |
| 16 | 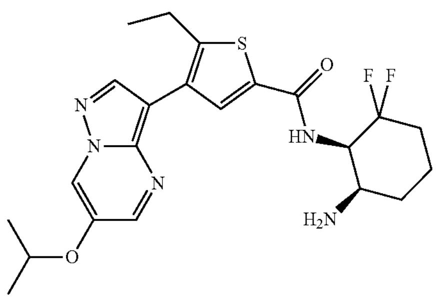 [SMILES: CCc1sc(C(=O)N[C@@H]2[C@H](N)CCCC2(F)F)cc1-c1cnn2cc(OC(C)C)cnc12] | N-[(1R,6S)-6-amino-2,2-difluorocyclohexyl]-5-ethyl-4-(6-(propan-2-yloxy)pyrazolo[1,5-a]pyrimidin-3-yl)thiophene-2-carboxamide | calc'd (M + H)$^+$ 464.2; found (M + H)$^+$ 464.1 |
| 17 | 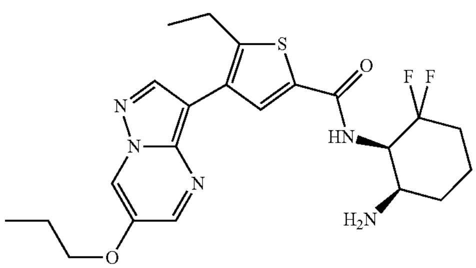 [SMILES: CCCOc1cnc2c(-c3cc(C(=O)N[C@@H]4[C@H](N)CCCC4(F)F)sc3CC)cnn2c1] | N-[(1R,6S)-6-amino-2,2-difluorocyclohexyl]-5-ethyl-4-(6-propoxypyrazolo[1,5-a]pyrimidin-3-yl)thiophene-2-carboxamide | calc'd (M + H)$^+$ 464.2; found (M + H)$^+$ 464.1 |
| 18 | 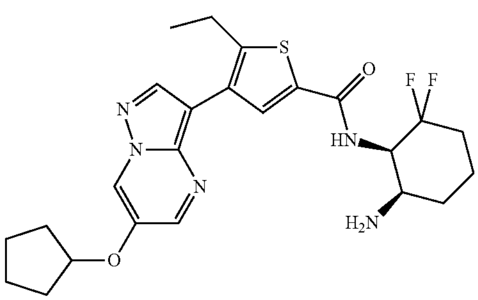 [SMILES: CCc1sc(C(=O)N[C@@H]2[C@H](N)CCCC2(F)F)cc1-c1cnn2cc(OC3CCCC3)cnc12] | N-[(1R,6R)-6-amino-2,2-difluorocyclohexyl]-4-[6-(cyclopentyloxy)pyrazolo[1,5-a]pyrimidin-3-yl]-5-ethylthiophene-2-carboxamide | calc'd (M + H)$^+$ 490.2; found (M + H)$^+$ 490.1 |
| 19 | 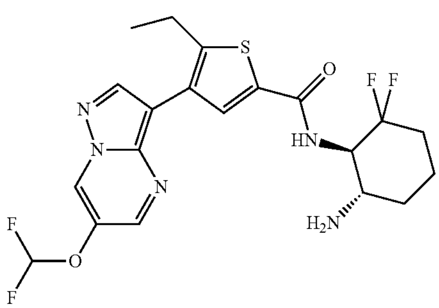 [SMILES: CCc1sc(C(=O)N[C@@H]2[C@@H](N)CCCC2(F)F)cc1-c1cnn2cc(OC(F)F)cnc12] | N-[(1R,6S)-6-amino-2,2-difluorocyclohexyl]-4-[6-(difluoromethoxy)pyrazolo[1,5-a]pyrimidin-3-yl]-5-ethylthiophene-2-carboxamide | calc'd (M + H)$^+$ 472.1; found (M + H)$^+$ 472.1 |

-continued

| Compound number | Structure | Name | MS |
|---|---|---|---|
| 20 | 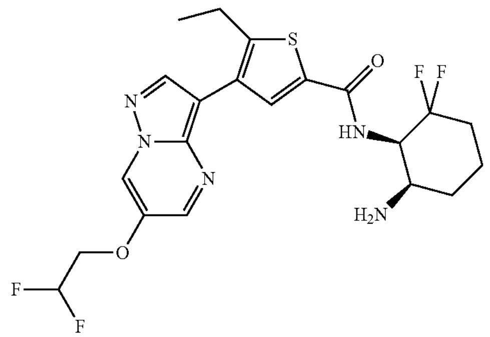 [SMILES: CCc1sc(C(=O)N[C@@H]2[C@H](N)CCCC2(F)F)cc1-c1cnn2cc(OCC(F)F)cnc12] | N-[(1R,6S)-6-amino-2,2-difluorocyclohexyl]-4-[6-(2,2-difluoroethoxy)pyrazolo[1,5-a]pyrimidin-3-yl]-5-ethylthiophene-2-carboxamide | calc'd (M + H)+ 486.2; found (M + H)+ 486.0 |
| 21 | 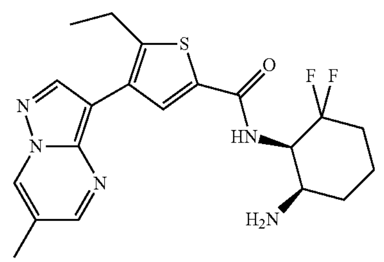 [SMILES: CCc1sc(C(=O)N[C@@H]2[C@H](N)CCCC2(F)F)cc1-c1cnn2cc(C)cnc12] | N-[(1R,6R)-6-amino-2,2-difluorocyclohexyl]-5-ethyl-4-(6-methylpyrazolo[1,5-a]pyrimidin-3-yl)thiophene-2-carboxamide | calc'd (M + H)+ 420.2; found (M + H)+ 420.0 |

Example 22

N-[(1R,6R)-6-Amino-2,2-difluorocyclohexyl]-5-ethyl-4-[6-(2,2,2-trifluoroethoxy)pyrazolo[1,5-a]pyrimidin-3-yl]thiophene-2-carboxamide Step 1.

tert-Butyl[(1R,2R)-2-({[5-ethyl-4-(6-hydroxypyrazolo[1,5-a]pyrimidin-3-yl)thiophen-2-yl]carbonyl}amino)-3,3-difluorocyclohexyl]carbamate

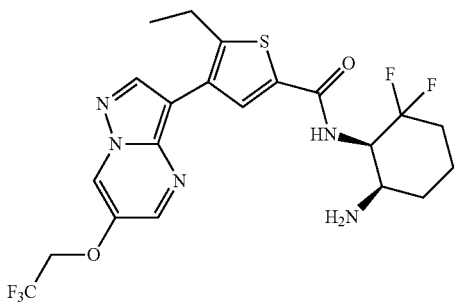 [SMILES: CCc1sc(C(=O)N[C@@H]2[C@H](N)CCCC2(F)F)cc1-c1cnn2cc(OCC(F)(F)F)cnc12]

tert-Butyl[(1R,2R)-2-({[4-(6-bromopyrazolo[1,5-a]pyrimidin-3-yl)-5-ethylthiophen-2-yl]carbonyl}amino)-3,3-difluorocyclohexyl]carbamate (0.151 g, 0.258 mmol) was dissolved in methanol (1.29 mL) and KOH (14.5 mg, 0.258 mmol) was added. The reaction was heated to 65° C. until conversion to the alcohol was complete. The reaction was then concentrated under reduced pressure. The remaining residue was mixed with dichloromethane, washed with saturated ammonium chloride (aq) twice and brine once. The organic layer was mixed with water and extracted 3× with dichloromethane. The combined organic layers were dried with sodium sulfate, filtered, and concentrated under reduced pressure to give the title compound (0.100 g, 0.192 mmol). LRMS (APCI) calc'd for (C$_{24}$H$_{29}$F$_2$N$_5$O$_4$S) [M+H]+, 522.2. found 522.0.

Step 2.

tert-Butyl{(1R,2R)-2-[({5-ethyl-4-[6-(2,2,2-trifluoroethoxy)pyrazolo[1,5-a]pyrimidin-3-yl]thiophen-2-yl}carbonyl)amino]-3,3-difluorocyclohexyl}carbamate

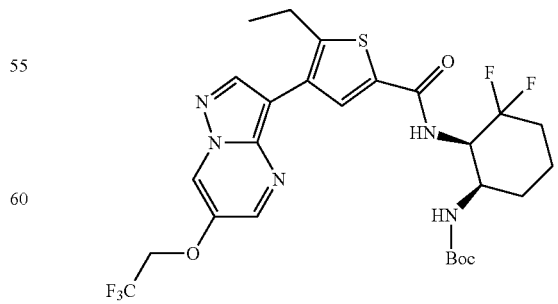

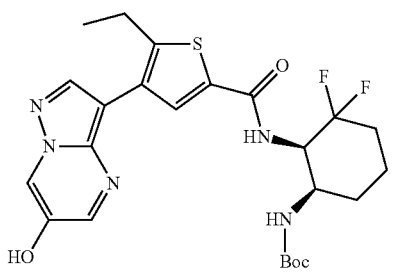 [SMILES: CCc1sc(C(=O)N[C@@H]2[C@H](NC(=O)OC(C)(C)C)CCCC2(F)F)cc1-c1cnn2cc(O)cnc12]

tert-Butyl[(1R,2R)-2-({[5-ethyl-4-(6-hydroxypyrazolo[1,5-a]pyrimidin-3-yl)thiophen-2-yl]carbonyl}amino)-3,3-difluorocyclohexyl]carbamate (81.0 mg, 0.155 mmol), 2,2,2-trifluoroethyl trifluoromethanesulfonate (40.3 mg, 0.173 mmol), and potassium carbonate (27.9 mg, 0.202 mmol) were placed in a sealed tube and heated to 40° C. for 6 h. The reaction mixture was cooled to room temperature and diluted with dichloromethane. The organic layer was washed with 1N NaOH (aq) once and 1N HCl (aq) twice. Water was added and the product extracted 3× with dichloromethane. The organic layers were combined, dried with sodium sulfate, filtered, and concentrated under reduced pressure. The crude product was purified via column chromatography (0-100% EtOAc/Hex) to give the title compound (34.0 mg, 0.056 mmol). LRMS (APCI) calc'd for ($C_{26}H_{30}F_5N_5O_4S$) [M+H]$^+$, 604.2; found 604.0.
Step 3.

N-[(1R,6R)-6-Amino-2,2-difluorocyclohexyl]-5-ethyl-4-[6-(2,2,2-trifluoroethoxy)pyrazolo[1,5-a]pyrimidin-3-yl]thiophene-2-carboxamide

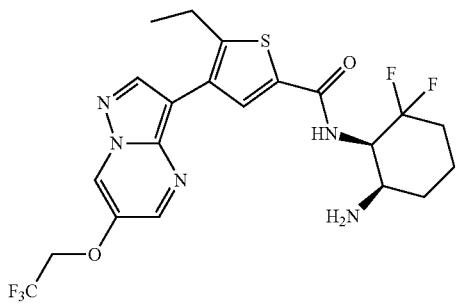 [SMILES: CCc1sc(C(=O)N[C@@H]2[C@H](N)CCCC2(F)F)cc1-c1cnn2cc(OCC(F)(F)F)cnc12]

tert-Butyl{(1R,2R)-2-[({5-ethyl-4-[6-(2,2,2-trifluoroethoxy)pyrazolo[1,5-a]pyrimidin-3-yl]thiophen-2-yl}carbonyl)amino]-3,3-difluorocyclohexyl}carbamate (34.0 mg, 0.056 mmol) was dissolved in dichloromethane (1.0 mL) and trifluoroacetic acid (0.100 mL, 1.30 mmol) was added. The reaction was stirred at 40° C. for 2 h. The reaction mixture was quenched with 1N KOH in MeOH and concentrated under reduced pressure. The residue was mixed with water and extracted 3× with dichloromethane. The organic layers were combined, dried with sodium sulfate, filtered, and concentrated under reduced pressure. The crude product was purified by column chromatography (0-20% MeOH/DCM) to give the title compound (23.0 mg, 0.046 mmol). LRMS (APCI) calc'd for ($C_{21}H_{22}F_5N_5O_2S$) [M+H]$^+$, 504.1; found 504.0. $^1$H NMR (CDCl$_3$, 500 MHz) δ 8.48 (s, 1H), 8.37 (s, 1H), 8.15 (s, 1H), 7.88 (s, 1H), 7.03 (s, 1H), 4.52 (m, 1H), 4.43 (d, J=7.8, 2H), 3.36 (s, 1H), 2.96 (q, J=7.2, 2H), 2.17 (s, 1H), 1.48-2.02 (m, 5H), 1.33 (t, J=7.3, 3H).
MARK 3 Assay MARK3 activity was assayed in vitro using a Cdc25C biotinylated peptide substrate (Cell Signalling Technologies). The phosphopeptide product was quantitated using a Homogenous Time-Resolved Fluorescence (HTRF) assay system (Park et al., 1999, *Anal. Biochem.* 269:94-104). The reaction mixture contained 50 mM HEPES/Tris-HCl, pH 7.4; 10 mM NaCl, 5 mM MgCl$_2$, 0.2 mM NaVO$_4$, 5 mM β-glycerol phosphate, 0.1% Tween-20, 2 mM dithiothreitol, 0.1% BSA, 10 μM ATP, 1 μM peptide substrate, and 10 nM recombinant MARK3 enzyme (University of Dundee) in a final volume of 12 μL. The buffer additionally contained protease inhibitor cocktail (Roche EDTA-free, 1 tab per 50 ml). The kinase reaction was incubated for 2 hours at 25° C., and then terminated with 3 μl Stop/Detection Buffer (50 mM HEPES, pH 7.0, 16.6 mM EDTA, 0.5M KF, 0.1% Tween-20, 0.1% BSA, 2 μg/ml SLX$^{ent}$ 665 (CISBIO), and 2 μg/mL Eu$^{3+}$ cryptate label antibody (CISBIO)). The reaction was allowed to equilibrate overnight at 0° C., and relative fluorescent units were read on an HTRF enabled plate reader (e.g. TECAN GENios Pro).

Inhibitor compounds were assayed in the reaction described above to determine compound IC$_{50}$s. Aliquots of compound dissolved in DMSO were added to the reaction wells in a third-log dilution series covering a range of 1 nM to 10 μM. Relative phospho substrate formation, read as HTRF fluorescence units, was measured over the range of compound concentrations and a titration curve generated.

Examples 1 to 22 were tested in the MARK3 assay described above and gave IC$_{50}$ values of 500 nM or less, typically 100 nM or less, and in some cases 10 nM less.
Caliper Kinase Selectivity Assay Kinase selectivity was profiled using Caliper mobility shift microfluidic technology on 96 and 144 kinase panel from ProfilePro Kits (plates 1-4 for 96 kinase panels and plates 1-4, 6, 7 for 144 kinase panels) (Caliper Life Sciences, Hopkinton, Mass.)

1) Remove reconstitution buffer and termination buffer from 4° C.

2) Remove and thaw DTT and protease inhibitor vials from −80° C.

3) To 50 ml reconstitution buffer bottle, add 50 uL of 1M DTT and 500 uL of 100× protease inhibitor.

4) Place reconstitution buffer, compound plate (26× concentrated), and termination buffer at 28° C.

5) Remove substrate plate from −80° C. and place at 28° C. on plate adapter

6) Wait 30 minutes.

7) Remove enzyme plate from −80° C. and place at 28° C. on adapter plate.

8) After 15 minutes, remove enzyme plate and spin at 1000 rpm for 1 minute. Remove seal.

9) Transfer 15 uL of reconstitution buffer to enzyme plate and mix.

10) Transfer 1 uL of compound and mix.

11) Pre-incubate for up to 15 minutes at 28° C.

12) At least 60 minutes after placing the substrate plate at 28° C., remove the substrate plate and spin at 500 rpm for 1 minute. Remove seal.

13) Add 10 uL of substrate to the enzyme plate, mix, spin at 500 rpm for 1 minute.

14) Cover plate and incubate at 28° C. on a third adaptor plate for 90 minutes.

15) Add 45 uL of termination buffer, mix if necessary and spin at 1000 rpm for 1 minute.

16) Read the plate on the Caliper EasyReader (click start button and follow instructions).

17) If plate cannot be read immediately, seal the plate and store at 4° C. until needed.

The following table provides IC$_{50}$ values in MARK3 assay and Caliper kinase selectivity profile for representative examples:

| Example | MARK3 IC$_{50}$ (nM) | Number of kinases with ≥50% inhibition at 100 nM | Number of kinases tested |
|---|---|---|---|
| Ex. 204 from WO 2009/014620 A1 | 1 | 14 | 93 |
| 4 | 27 | 0 | 91 |
| 6 | 73 | 0 | 140 |
| 9 | 3 | 8 | 93 |
| 10 | 5 | 6 | 93 |
| 15 | 2 | 3 | 93 |

As shown above, compounds of the invention showed higher selectivity against other kinases as compared Ex. 204 disclosed in WO 2009/014620 A1.

pTau(S262) Cell Biochemical and Functional Assay

The cell biochemical potency of the above described MARK inhibitors can be evaluated by measuring their ability to block the phosphorylation of Tau at S262 in primary cell culture of rat cortical neurons induced by the action of Okadaic acid.

Reagents:
Neurobasal (Invitrogen, cat. 21103-049)
B27 (Invitrogen, cat. 17504-044)
L-Glutamine (Invitrogen, cat. 25030-081)
Penicillin-Streptomycin (Invitrogen, cat. 15140)
Papain, sterile lyophilized (Worthington, cat. NC9212788) 10 mL 1M Hepes added for 10× solution
Tissue Culture plates:
  384 well: BD FALCON BD BIOCOAT Poly-D-Lysine Black/Clear Microtest, Tissue-Culture Treated Polystyrene (cat. 354663)
E18 Primary Rat Cortical Cells: BrainBits, cat. cx2
Stock Media (NB): Neurobasal+B-27 (1:50)+0.5 mM L-Glutamine+1% Pen/Strep Preparation of Isolated Neurons
1. Store tissue at 4° C. (1-2 days) until ready to use.
2. When ready to plate, make up 2 mL of enzymatic solution in Hibernate-Ca containing 1× papain. Filter sterile solution with 0.2 μm filter.
3. Transfer 2 mL of medium from tissue tube into 15 mL falcon tube while not disturbing tissue. Save media.
4. Add 2 mL enzymatic media (2) to tissue. Incubate for 30' at 37° C.
5. Remove enzymatic solution while not disturbing tissue. Add back 1 mL of media from (3).
6. Using pipettor with sterile plastic tip, triturate ~10 times until most of the cells are dispersed.
7. Let undispersed pieces settle by gravity 1 minute.
8. Transfer dispersed cells (supernatant) into 15 mL falcon tube containing 1 mL media from (3). Gently mix cells by swirling.
9. Spin cells at 1,100 rpm for 1 minute. Remove supernatant.
10. Flick tube to loosen cell pellet. Resuspend cells in 5 mL of NB.
11. Transfer to new 50 mL falcon tube using 40 μm cell strainer. Rinse 15 mL falcon tube with 5 mL media, add to strainer.
12. Count cells using hemacytometer.
13. Dilute cells to 7,000 cells/100 μL/well in NB.
14. Incubate cells at 37° C. with 5% CO$_2$.
  a. 4 DIV: Replace ½ volume (50 μL) NB per well.
  b. 6 DIV: eurite Assay.

Tissue Culture/Compound Treatment
Primary rat cortical neurons plated about 6Kcells/well in 384-well black/clear bottom Poly D-Lysine coated BD Falcon Biocoat plates.
Media: Neurobasal+1×B27+2 mM L-Glutamine (+10% FBS) at time of plating
Cells maintained at 37° C. and 5% CO$_2$ for 6 days in culture, w/½ media change every 3-4 days.
Compound treatment:
  Prepare first plate: 200× compound in 100% DMSO with subsequent 3 fold serial dilution
  Prepare intermediate plate: 1:40 dilution of 200× compound in media (2.5% DMSO)
  Add 5× compound to cell in media at 1:5 dilution (0.5% final DMSO)
  Incubate for 30 min. at 37° C.
Okadaic Acid (OA) Treatment:
  Dilute OA stock (240 μM in 100% DMSO) to 6× final concentration in media (0.5% DMSO)
  Add 6×OA to cells at 1:6 dilution (200 nM final). Incubate for 1.5 hrs. at 37° C.

Fix and Immunostaining
Fix: 1% PFA, diluted in PBS
  Wash 1× with PBS, residual 30 ul/well.
  Add 30 4/well warmed 2% PFA and incubate 30 min. at RT (1% PFA final)

Wash 3× with PBS, 30 μl/well residual
Permeabilize & Block.
  Add 30 μl/well PBS+0.2% Triton X-100+10% normal
    goat serum (0.1% Triton & 5% NGS final).
  Incubate 1 hr at RT or O/N at 4° C.
Wash 3× with PBS, 30 μL/well residual
Primary antibody: add 304/well 2× final concentration
  antibody diluted in PBS
Mouse anti-tau-3R
  Rabbit anti-tau-pS$^{262}$
  Incubate O/N at 4° C.
Wash 4× with PBS, 30 μL/well residual
Secondary antibody & nuclear staining: add 30 μl/well 2×
  final concentration stain diluted in PBS
  AlexaFluor goat anti mouse 488
  AlexaFluor goat anti rabbit 594
  Hoechst
  Incubate in dark 1 hr. at RT
Wash 4× with PBS 30 μl/well residual, protect from light
Acquire images in INCell Analyzer 1000 & Opera.
  Examples 1 to 22 were tested for inhibition of phosphorylation of Tau at S262 in the above described assay and gave IC$_{50}$ values of 10 μM or less, typically 1000 nM or less, and in some cases 250 nM less.

What is claimed is:

1. A compound of formula I:

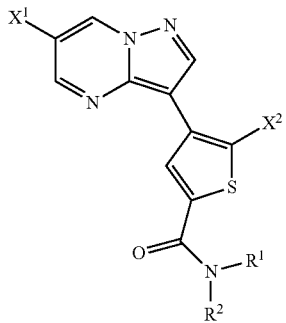

I or a pharmaceutically acceptable salt or hydrate thereof;
wherein:
  $X^1$ is selected from the group consisting of: H, halogen, $C_{1-6}$alkyl, $C_{2-6}$alkenyl, $C_{2-6}$alkynyl, $C_{3-6}$cycloalkyl, $C_{1-6}$alkoxy, —C(O)—OC$_{1-4}$alkyl, $C_{3-6}$cycloalkoxy, CN and N(R$^3$)$_2$, wherein said $C_{1-6}$alkyl, $C_{2-6}$alkenyl, $C_{2-6}$alkynyl, $C_{3-6}$cycloalkyl, $C_{1-6}$alkoxy, —C(O)—OC$_{1-4}$alkyl and $C_{3-6}$cycloalkoxy are optionally substituted up to the maximum number of substitutable positions with halogen;
  $X^2$ is selected from the group consisting of: H, halogen, $C_{3-6}$cycloalkyl, $C_{1-6}$alkyl, $C_{2-6}$alkenyl, $C_{2-6}$alkynyl, $C_{3-6}$cycloalkenyl, —CN, nitro and N(R$^3$)$_2$; said $C_{1-6}$alkyl optionally substituted with up to 3 halogen atoms and said $C_{2-6}$alkenyl and $C_{2-6}$alkynyl optionally substituted with up to 3 R$^5$ groups;
  $R^1$ represents H or $C_{1-4}$alkyl which is optionally substituted with OH, CN, CF$_3$, $C_{1-4}$alkoxy, amino, $C_{1-4}$alkylamino or di($C_{1-4}$alkyl)amino;
  $R^2$ is selected from:
  (i) H;
  (ii) $C_{1-8}$alkyl or $C_{2-8}$alkenyl, either of which optionally bears up to 3 substituents independently selected from halogen, OH, CN, CF$_3$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$, NR$^3$SO$_2$R$^4$ and phenyl, said phenyl bearing 0 to 5 halogen substituents; and
  (iii) $C_{3-10}$cycloalkyl, $C_{3-10}$cycloalkylC$_{1-4}$alkyl, Het, HetC$_{1-4}$alkyl, aryl or arylC$_{1-4}$alkyl, any of which optionally bears up to 4 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$, NR$^3$SO$_2$R$^4$ and —P(O)—(OR$^3$)$_2$; where "aryl" refers to phenyl or 5- or 6-membered heteroaryl, either of which phenyl or heteroaryl is optionally fused to a 5- or 6-membered carbocycle or heterocycle, "Het" refers to a nonaromatic or partially aromatic mono -or bicyclic heterocyclic system of up to 10 ring atoms and $C_{3-10}$cycloalkyl and the cyclic portion of $C_{3-10}$cycloalkylC$_{1-4}$alkyl may be fused with phenyl or a 5- or 6-membered heteroaryl;
  or $R^1$ and $R^2$ together may complete a mono- or bicyclic heterocyclic system of up to 10 ring atoms which optionally bears up to 3 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$ and NR$^3$SO$_2$R$^4$;
  each R$^3$ independently represents H or $C_{1-6}$alkyl which is optionally substituted with up to 3 halogen atoms or with OH, CN, CF$_3$, $C_{1-4}$alkoxy, amino, $C_{1-4}$alkylamino or di($C_{1-4}$alkyl)amino;
  R$^4$ has the same definition as R$^3$ except that R$^4$ is not H; and
  R$^5$ is selected from the group consisting of: phenyl, hydroxy, $C_{3-6}$cycloalkyl, and $C_{1-4}$alkoxy.

2. The compound according to claim 1 wherein $X^2$ is $C_{1-4}$alkyl.

3. The compound according to claim 2 wherein R$^2$ is $C_{3-10}$cycloalkyl bearing up to 3 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$ and NR$^3$SO$_2$R$^4$.

4. The compound according to claim 2 wherein R$^2$ is cyclohexyl bearing up to 3 substituents independently selected from halogen, OH, oxo, CN, CF$_3$, R$^4$, OR$^3$, SR$^4$, SO$_2$R$^4$, SO$_2$N(R$^3$)$_2$, COR$^3$, CO$_2$R$^3$, CON(R$^3$)$_2$, N(R$^3$)$_2$, NR$^3$COR$^4$ and NR$^3$SO$_2$R$^4$.

5. The compound according to claim 1 of Formula Ia

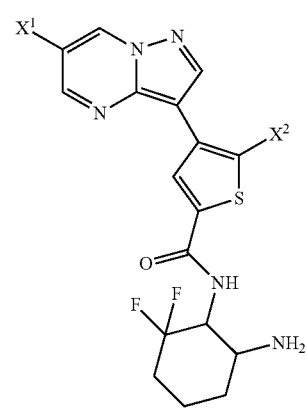

Ia or a pharmaceutically acceptable salt or hydrate thereof;
wherein:
  $X^1$ is selected from the group consisting of: halogen, $C_{1-6}$alkyl, $C_{3-6}$cycloalkyl, $C_{1-6}$alkoxy, —C(O)—OC$_{1-}$ 4alkyl and $C_{3-6}$cycloalkoxy, wherein said $C_{1-6}$alkyl and $C_{1-6}$alkoxy are optionally substituted up to the maximum number of substitutable positions with fluoro; and $X^2$ is halogen, methyl or ethyl.

6. The compound according to claim 5 wherein: $X^1$ is selected from the group consisting of: chloro, methyl, trifluoromethyl, methoxy, difluoromethoxy, trifluoromethoxy, ethoxy, propoxy, isopropoxy, cyclopentyloxy, 2,2-difluoroethoxy, 2,2,2-trifluoroethoxy and methoxycarbonyl.

7. A compound selected from the group consisting of:
N-[6-amino-2,2,difluorocyclohexyl]-4-(6-chloropyrazolo[1,5-a]pyrimidin-3-yl)-5-chlorothiophene-2-carboxamide;
N-[6-amino-2,2,difluorocyclohexyl]-4-(6-chloropyrazolo[1,5-a]pyrimidin-3-yl)-5-methylthiophene-2-carboxamide;
N-[6-amino-2,2-difluorocyclohexyl]-4-(6-chloropyrazolo[1,5-a]pyrimidin-3-yl)-5-ethylthiophene-2-carboxamide;
N-[6-amino-2,2-difluorocyclohexyl]-5-ethyl-4-[6-(trifluoromethyl)pyrazolo[1,5-a]pyrimindin-3-yl]thiophene-2-carboxamide;
Methyl-3-(5-{[6-amino-2,2-difluorocyclohexyl]carbamoyl}-2-methylthiophen-3-yl)pyrazolo[1,5-a]pyrimidine-6-carboxylate;
N-[6-amino-2,2-difluorocyclohexyl]-4-[6-(difluoromethoxy)pyrazolo[1,5-a]pyrimidin-3-yl]-5-methylthiophene-2-carboxamide;
N-[6-amino-2,2-difluorocyclohexyl]-4-(6-methoxypyrazolo[1,5-a]pyrimidin-3-yl)-5-methylthiophene-2-carboxamide;
N-[6-amino-2,2-difluorocyclohexyl]-4-[6-(difluoromethoxy)pyrazolo[1,5-a]pyrimidin-3-yl]-5-ethylthiophene-2-carboxamide;
N-[6-amino-2,2-difluorocyclohexyl]-5-ethyl-4-(6-methoxypyrazolo[1,5-a]pyrimidin-3-yl)thiophene-2-carboxamide;
N-[6-amino-2,2-difluorocyclohexyl]-4-(6-ethoxypyrazolo[1,5-a]pyrimidin-3-yl)-5-ethylthiophene-2-carboxamide;
N-[6-amino-2,2-difluorocyclohexyl]-5-ethyl-4-(6-(propan-2-yloxy)pyrazolo[1,5-a]pyrimidin-3-yl)thiophene-2-carboxamide;
N-[6-amino-2,2-difluorocyclohexyl]-5-ethyl-4-(6-propoxypyrazolo[1,5-a]pyrimidin-3-yl)thiophene-2-carboxamide;
N-[6-amino-2,2-difluorocyclohexyl]-4-[6-(cyclopentyloxy)pyrazolo[1,5-a]pyrimidin-3-yl]-5-ethylthiophene-2-carboxamide;
N-[6-amino-2,2-difluorocyclohexyl]-4-[6-(2,2-difluoroethoxy)pyrazolo[1,5-a]pyrimidin-3-yl]-5-ethylthiophene-2-carboxamide;
N-[6-amino-2,2-difluorocyclohexyl]-5-ethyl-4-(6-methylpyrazolo[1,5-a]pyrimidin-3-yl)thiophene-2-carboxamide; and
N-[6-Amino-2,2-difluorocyclohexyl]-5-ethyl-4-[6-(2,2,2-trifluoroethoxy)pyrazolo[1,5-a]pyrimidin-3-yl]thiophene-2-carboxamide;
or a pharmaceutically acceptable salt of any of the foregoing compounds.

8. A pharmaceutical composition comprising a compound of formula I as defined in claim 1 or a pharmaceutically acceptable salt or hydrate thereof, and a pharmaceutically acceptable carrier.

9. A method for treating a neurodegenerative disease associated with hyperphosphorylation of tau in a human patient, said method comprising administering to said patient an effective amount of a compound of formula I as defined in claim 1 or a pharmaceutically acceptable salt or hydrate thereof.

10. The method according to claim 9 wherein the neurodegenerative disease is Alzheimer's disease.

11. A method for reducing the production of hyperphosphorylated tau in a human patient, said method comprising administering to said patient an effective amount of a compound of formula I as defined in claim 1 or a pharmaceutically acceptable salt or hydrate thereof.

\* \* \* \* \*